United States Patent
Borsody

(10) Patent No.: US 9,339,645 B2
(45) Date of Patent: May 17, 2016

(54) MODULATING FUNCTION OF THE FACIAL NERVE SYSTEM OR RELATED NEURAL STRUCTURES VIA THE EAR

(75) Inventor: Mark Klingler Borsody, San Francisco, CA (US)

(73) Assignee: Nervive, Inc., Orinda, CA (US)

( * ) Notice: Subject to any disclaimer, the term of this patent is extended or adjusted under 35 U.S.C. 154(b) by 0 days.

(21) Appl. No.: 13/096,889

(22) Filed: Apr. 28, 2011

(65) Prior Publication Data

US 2011/0270361 A1 Nov. 3, 2011

Related U.S. Application Data

(60) Provisional application No. 61/397,462, filed on Jun. 14, 2010, provisional application No. 61/330,366, filed on May 2, 2010.

(51) Int. Cl.
*A61N 1/36* (2006.01)
*A61N 1/05* (2006.01)
*A61N 1/372* (2006.01)

(52) U.S. Cl.
CPC ............ *A61N 1/0526* (2013.01); *A61N 1/0541* (2013.01); *A61N 1/36* (2013.01); *A61N 1/36017* (2013.01); *A61N 1/36025* (2013.01); *A61N 1/37223* (2013.01)

(58) Field of Classification Search
CPC . A61N 1/0526; A61N 1/0541; A61N 1/0504; A61N 1/36; A61N 2/006
USPC .................................. 607/55–57, 2, 62, 116
See application file for complete search history.

(56) References Cited

U.S. PATENT DOCUMENTS 2,876,767 A * 3/1959 Wasserman .................... 128/865
3,629,521 A * 12/1971 Puharich et al. ................ 607/56
(Continued)

FOREIGN PATENT DOCUMENTS

CA 1 135 348 A1 11/1982
CA 2 021 506 A1 7/1990
(Continued)

OTHER PUBLICATIONS

Bar-Shir, A. et al., "Late Stimulation of the Sphenopalatine-Ganglion in Ischemic Rats: Improvement in N-Acetyl-Aspartate Levels and Diffusion Weighted Imaging Characteristcs as Seen by MR," *Journal of Magnetic Resonance Imaging*, 2010, pp. 1355-1363, vol. 31.
(Continued)

Primary Examiner — William Levicky
(74) Attorney, Agent, or Firm — Fenwick & West LLP

(57) ABSTRACT

Stimulation of the facial nerve system (e.g., electrically, electromagnetically, etc.) in stroke patients will cause dilation of occluded arteries and dilation of surrounding arteries, allowing for blood flow to circumvent the obstruction and reach previously-deprived tissue. The device approaches the facial nerve and its branches in the vicinity of the ear. In use, the device can be inserted into the ear canal or placed in proximity to the ear in order to stimulate the facial nerve system without puncturing the tympanic membrane (e.g., using an electromagnetic field). The device can also be advanced into the middle ear through a puncture created in the tympanic membrane. Branches of the facial nerve in the middle ear can then be stimulated directly (e.g., by application of electrical current). The device can be used in the emergency treatment of acute stroke or as chronically-implanted/inserted variations for long-term maintenance of blood flow to the brain and stroke prevention.

19 Claims, 26 Drawing Sheets

(56) References Cited

U.S. PATENT DOCUMENTS

| | | | |
|---|---|---|---|
| 4,044,774 A * | 8/1977 | Corbin et al. | 607/117 |
| 4,696,287 A * | 9/1987 | Hortmann et al. | 607/57 |
| 5,116,304 A | 5/1992 | Cadwell | |
| 5,441,495 A | 8/1995 | Liboff et al. | |
| 5,461,215 A | 10/1995 | Haldeman | |
| 5,607,461 A * | 3/1997 | Lathrop | 607/75 |
| 5,922,016 A | 7/1999 | Wagner | |
| 5,991,664 A * | 11/1999 | Seligman | 607/60 |
| 6,078,838 A | 6/2000 | Rubinstein | |
| 6,093,417 A | 7/2000 | Petrus | |
| 6,179,770 B1 | 1/2001 | Mould | |
| 6,179,771 B1 | 1/2001 | Mueller | |
| 6,179,772 B1 | 1/2001 | Blackwell | |
| 6,213,933 B1 | 4/2001 | Lin | |
| 6,310,961 B1 * | 10/2001 | Oliveira et al. | 381/328 |
| 6,408,855 B1 * | 6/2002 | Berrang et al. | 128/898 |
| 6,425,852 B1 | 7/2002 | Epstein et al. | |
| 6,468,199 B1 | 10/2002 | Satou et al. | |
| 6,488,617 B1 | 12/2002 | Katz | |
| 6,526,318 B1 | 2/2003 | Ansarinia | |
| 6,551,233 B2 | 4/2003 | Perreault et al. | |
| 6,629,399 B2 | 10/2003 | Sarles et al. | |
| 6,663,556 B2 | 12/2003 | Barker | |
| 6,849,040 B2 | 2/2005 | Ruohonen et al. | |
| 6,853,858 B2 | 2/2005 | Shalev | |
| 6,900,420 B2 | 5/2005 | Markegård et al. | |
| 6,926,660 B2 | 8/2005 | Miller | |
| 7,103,417 B1 * | 9/2006 | Segel et al. | 607/57 |
| 7,117,033 B2 | 10/2006 | Shalev et al. | |
| 7,120,489 B2 | 10/2006 | Shalev et al. | |
| 7,146,209 B2 | 12/2006 | Gross et al. | |
| 7,146,227 B2 * | 12/2006 | Dadd et al. | 607/137 |
| 7,149,574 B2 | 12/2006 | Yun et al. | |
| 7,340,298 B1 | 3/2008 | Barbut | |
| 7,363,076 B2 | 4/2008 | Yun et al. | |
| 7,367,936 B2 | 5/2008 | Myers et al. | |
| 7,396,326 B2 | 7/2008 | Ghiron et al. | |
| 7,407,478 B2 | 8/2008 | Zangen et al. | |
| 7,519,435 B2 * | 4/2009 | Parker et al. | 607/137 |
| 7,561,919 B2 | 7/2009 | Shalev et al. | |
| 7,580,754 B2 * | 8/2009 | Zhang et al. | 607/55 |
| 7,591,776 B2 | 9/2009 | Phillips et al. | |
| 7,591,779 B2 * | 9/2009 | Kalinowski et al. | 600/23 |
| 7,601,115 B2 | 10/2009 | Riehl | |
| 7,636,597 B2 | 12/2009 | Gross et al. | |
| 7,640,062 B2 | 12/2009 | Shalev | |
| 7,658,704 B2 | 2/2010 | Fox et al. | |
| 7,684,858 B2 | 3/2010 | He et al. | |
| 7,684,859 B2 | 3/2010 | Shalev et al. | |
| 7,711,432 B2 | 5/2010 | Thimineur et al. | |
| 7,771,341 B2 | 8/2010 | Rogers | |
| 7,854,232 B2 | 12/2010 | Aho et al. | |
| 7,946,973 B2 | 5/2011 | Peterchev | |
| 7,973,635 B2 | 7/2011 | Baarman et al. | |
| 7,976,451 B2 | 7/2011 | Zangen et al. | |
| 7,998,053 B2 | 8/2011 | Aho | |
| 8,052,591 B2 | 11/2011 | Mishelevich et al. | |
| 8,267,850 B2 | 9/2012 | Schneider et al. | |
| 8,277,371 B2 | 10/2012 | Zangen et al. | |
| 8,388,510 B2 | 3/2013 | Zangen et al. | |
| 8,396,566 B2 * | 3/2013 | Kassab et al. | 607/119 |
| 8,412,342 B2 * | 4/2013 | Zhang et al. | 607/57 |
| 8,460,167 B2 | 6/2013 | Chornenky et al. | |
| 8,523,753 B2 | 9/2013 | Schneider et al. | |
| 8,545,378 B2 | 10/2013 | Peterchev | |
| 8,591,392 B2 | 11/2013 | Bentwich et al. | |
| 8,723,628 B2 | 5/2014 | Mishelevich et al. | |
| 8,771,163 B2 | 7/2014 | Zangen et al. | |
| 8,795,148 B2 | 8/2014 | Schneider et al. | |
| 2001/0031906 A1 | 10/2001 | Ishikawa et al. | |
| 2002/0026125 A1 | 2/2002 | Leysieffer | |
| 2002/0151886 A1 * | 10/2002 | Wood | 606/41 |
| 2003/0004393 A1 | 1/2003 | Ewing et al. | |
| 2003/0195588 A1 | 10/2003 | Fischell et al. | |
| 2005/0027251 A1 * | 2/2005 | Masters | 604/114 |
| 2005/0222486 A1 | 10/2005 | Shin et al. | |
| 2005/0288664 A1 * | 12/2005 | Ford et al. | 606/41 |
| 2006/0122675 A1 | 6/2006 | Libbus et al. | |
| 2006/0162952 A1 | 7/2006 | Olbrich et al. | |
| 2006/0187607 A1 | 8/2006 | Mo | |
| 2006/0287689 A1 * | 12/2006 | Debruyne et al. | 607/57 |
| 2007/0118197 A1 * | 5/2007 | Loeb | 607/116 |
| 2008/0027513 A1 | 1/2008 | Carbunaru | |
| 2008/0082141 A1 * | 4/2008 | Risi | 607/57 |
| 2008/0097549 A1 * | 4/2008 | Colbaugh et al. | 607/55 |
| 2008/0154343 A1 | 6/2008 | Li et al. | |
| 2008/0224808 A1 | 9/2008 | Ghiron et al. | |
| 2008/0262287 A1 | 10/2008 | Dussau | |
| 2008/0262468 A1 | 10/2008 | Clifford et al. | |
| 2009/0018384 A1 | 1/2009 | Boyden et al. | |
| 2009/0099405 A1 | 4/2009 | Schneider et al. | |
| 2009/0108969 A1 | 4/2009 | Sims et al. | |
| 2009/0131739 A1 * | 5/2009 | Shalev | 600/13 |
| 2009/0174407 A1 | 7/2009 | Han et al. | |
| 2009/0187098 A1 | 7/2009 | Makower et al. | |
| 2010/0016650 A1 | 1/2010 | Phillips et al. | |
| 2010/0094076 A1 | 4/2010 | Phillips | |
| 2010/0113959 A1 | 5/2010 | Pascual-Leone et al. | |
| 2010/0114184 A1 | 5/2010 | Degtyar et al. | |
| 2010/0193506 A1 | 8/2010 | Nagai et al. | |
| 2010/0286470 A1 | 11/2010 | Schneider et al. | |
| 2010/0331602 A1 | 12/2010 | Mishelevich et al. | |
| 2011/0082326 A1 | 4/2011 | Mishelevich et al. | |
| 2011/0125203 A1 | 5/2011 | Simon et al. | |
| 2011/0218381 A1 | 9/2011 | Ruohonen | |
| 2011/0263925 A1 | 10/2011 | Bratton | |
| 2012/0101366 A1 | 4/2012 | Ruohonen et al. | |
| 2012/0149969 A1 | 6/2012 | Farone | |
| 2013/0096363 A1 | 4/2013 | Schneider et al. | |
| 2013/0267763 A1 | 10/2013 | Schneider et al. | |
| 2013/0278369 A1 | 10/2013 | Shepard et al. | |
| 2013/0304159 A1 | 11/2013 | Simon et al. | |
| 2013/0317281 A1 | 11/2013 | Schneider et al. | |
| 2014/0081072 A1 | 3/2014 | Huang et al. | |
| 2014/0085031 A1 | 3/2014 | Nomura et al. | |
| 2014/0163305 A1 | 6/2014 | Watterson | |

FOREIGN PATENT DOCUMENTS

| | | |
|---|---|---|
| CA | 2 608 084 A1 | 11/2006 |
| CA | 2 610 991 A1 | 12/2006 |
| CN | 86105171 A | 3/1987 |
| CN | 101366666 A | 2/2009 |
| CN | 101985058 A | 3/2011 |
| CN | 102013579 A | 4/2011 |
| CN | 202605538 U | 12/2012 |
| CN | 202637725 U | 1/2013 |
| CN | 202961526 U | 6/2013 |
| DE | 10046275 A1 | 3/2002 |
| EP | 0 214 527 A1 | 3/1987 |
| EP | 0 408 230 A2 | 1/1991 |
| EP | 1 671 672 A1 | 6/2006 |
| EP | 1 890 762 A2 | 2/2008 |
| EP | 1 145 738 B1 | 11/2008 |
| EP | 1 890 615 A4 | 9/2009 |
| EP | 2 384 223 A2 | 11/2011 |
| EP | 2 520 334 A1 | 11/2012 |
| EP | 2 666 515 A1 | 11/2013 |
| JP | S62-44250 | 2/1987 |
| JP | 2003-503119 A | 1/2003 |
| JP | 2003-180847 A | 7/2003 |
| JP | 2006-515999 | 6/2006 |
| JP | 2008-522725 A | 7/2008 |
| JP | 2008-528145 A | 7/2008 |
| JP | 2010-213979 A | 9/2010 |
| RU | 2012 115 948 A | 10/2013 |
| WO | WO 95/25417 A1 | 9/1995 |
| WO | WO 97/00639 A1 | 1/1997 |

(56) References Cited

FOREIGN PATENT DOCUMENTS

| | | |
|---|---|---|
| WO | WO 01/00273 A1 | 1/2001 |
| WO | WO 01/97095 | 12/2001 |
| WO | WO 01/97905 | 12/2001 |
| WO | WO 02/32504 A2 | 4/2002 |
| WO | WO 02/089902 A2 | 11/2002 |
| WO | WO 03/026478 | 4/2003 |
| WO | WO 03/090863 A1 | 11/2003 |
| WO | WO 2004/036603 A1 | 4/2004 |
| WO | WO 2004/043217 | 5/2004 |
| WO | WO 2004/043218 | 5/2004 |
| WO | WO 2004/043334 | 5/2004 |
| WO | WO 2004/045242 | 5/2004 |
| WO | WO 2004/087255 A1 | 10/2004 |
| WO | WO 2005/002346 | 1/2005 |
| WO | WO 2005/030025 | 4/2005 |
| WO | WO 2006/014896 | 2/2006 |
| WO | WO 2006/021957 | 3/2006 |
| WO | WO 2006/040690 | 4/2006 |
| WO | WO 2006/057734 | 6/2006 |
| WO | WO 2006/076708 | 7/2006 |
| WO | WO 2006/078924 | 7/2006 |
| WO | WO 2006/083675 | 8/2006 |
| WO | WO 2006/119512 | 11/2006 |
| WO | WO 2006/134598 A3 | 12/2006 |
| WO | WO 2006/135853 | 12/2006 |
| WO | WO 2007/137335 | 12/2007 |
| WO | WO 2008/030485 | 3/2008 |
| WO | WO 2008/048471 A2 | 4/2008 |
| WO | WO 2008/052166 | 5/2008 |
| WO | WO 2008/112915 | 9/2008 |
| WO | WO 2008/130533 A2 | 10/2008 |
| WO | WO 2008/150963 | 12/2008 |
| WO | WO 2009/011939 | 1/2009 |
| WO | WO 2009/013881 A1 | 1/2009 |
| WO | WO 2009/033144 A2 | 3/2009 |
| WO | WO 2009/033150 A1 | 3/2009 |
| WO | WO 2009/033192 A1 | 3/2009 |
| WO | WO 2009/037689 | 3/2009 |
| WO | WO 2009/042863 A1 | 4/2009 |
| WO | WO 2009/047370 | 4/2009 |
| WO | WO 2009/100633 A1 | 8/2009 |
| WO | WO 2009/138428 | 11/2009 |
| WO | WO 2009/143171 | 11/2009 |
| WO | WO 2010/014894 | 2/2010 |
| WO | WO 2010/033909 | 3/2010 |
| WO | WO 2010/049576 A1 | 5/2010 |
| WO | WO 2010/062622 | 6/2010 |
| WO | WO 2010/080879 A2 | 7/2010 |
| WO | WO 2011/060699 A1 | 5/2011 |
| WO | WO 2012/045079 A9 | 4/2012 |
| WO | WO 2012/048319 A2 | 4/2012 |
| WO | WO 2012/090068 A2 | 7/2012 |
| WO | WO 2012/117166 A1 | 9/2012 |
| WO | WO 2013/006670 A2 | 1/2013 |
| WO | WO 2013/116235 A1 | 8/2013 |
| WO | WO 2013/126176 A1 | 8/2013 |
| WO | WO 2014/022236 A1 | 2/2014 |
| WO | WO 2014/097571 A1 | 6/2014 |

OTHER PUBLICATIONS

Brainsgate, "Ischemic Stroke System," 2005, two pages. [Online] [Retrieved Oct. 19, 2011] Retrieved from the Internet <URL:http://www.brainsgate.com/eng/page.php?id=11&instance_id=8>.

Khurana, D. et al., "Implant for Augmentation of Cerebral Blood Flow Trial 1: A pilot Study Evaluating the Safety and Effectiveness of the Ischaemic Stroke System for Treatment of Acute Ischaemic Stroke," *International Journal of Stroke*, Dec. 2009, pp. 480-485, vol. 4.

PCT International Search Report and Written Opinion, PCT Application No. PCT/US2011/034378, Aug. 8, 2011, seven pages.

Yarnitsky, D. et al., "Blood-brain Barrier Opened by Stimulation of the Parasympathetic Sphenopalatine Ganglion: A New Method for Macromolecule Deliver to the Brain," *Journal of Neurosurgery*, 2004, pp. 303-309, vol. 101.

Yarnitsky, D. et al., "Increased BBB Permeability by Parasympathetic Sphenopalatine Ganglion Stimulation in Dogs," *Brain Research*, 2004, five pages.

Yarnitsky, D. et al., "Reversal of Cerebral Vasospasm by Sphenopalatine Ganglion Stimulation in a Dog Model of Subarachnoid Hemorrahage," Surgical Neurology, 2005, pp. 5-11, vol. 64.

PCT International Search Report and Written Opinion, PCT Application No. PCT/US2012/067801, Apr. 19, 2013, twelve pages.

European Patent Office, Search Report and Opinion, European Patent Application No. 11778023.9, Jul. 31, 2014, eight pages.

Goadsby, P.J., "Characteristics of facial nerve-elicited cerebral vasodilatation determined using laser Doppler flowmetry," Database Accession No. NLM1992824, Jan. 1991, XP002711162, Database Medline, U.S. National Library of Medicine (NLM), Bethesda, Maryland, U.S.

Japanese Patent Office, Office Action, Japanese Patent Application No. 2013-509125, Oct. 1, 2014, eight pages.

State Intellectual Property Office of the People's Republic of China, First Office Action, Chinese Patent Application No. 201180022239.3, Apr. 4, 2014, fifteen pages.

Stjernschantz, J. et al., "Vasomotor effects of facial nerve stimulation: noncholinergic vasodilation in the eye," *Acta Physiologica Scandinavica*, May 1, 1980, pp. 45-50, vol. 109, No. 1, Scandinavian Physiological Society.

United States Office Action, U.S. Appl. No. 13/692,226, Jun. 10, 2014, nineteen pages.

United States Office Action, U.S. Appl. No. 13/692,226, Sep. 9, 2014, twenty-three pages.

Israel Patent Office, Office Action, Israeli Patent Application No. 222750, May 3, 2015, six pages.

Australian Government, IP Australia, Patent Examination Report No. 1, Patent Examination No. 2011248487, Feb. 17, 2015, three pages.

European Patent Office, Search Report and Opinion, European Patent Application No. 12856454.9, Oct. 19, 2015, six pages.

State Intellectual Property Office of the People's Republic of China, First Office Action, Chinese Patent Application No. 2012800598917, Mar. 19, 2015, sixteen pages.

\* cited by examiner

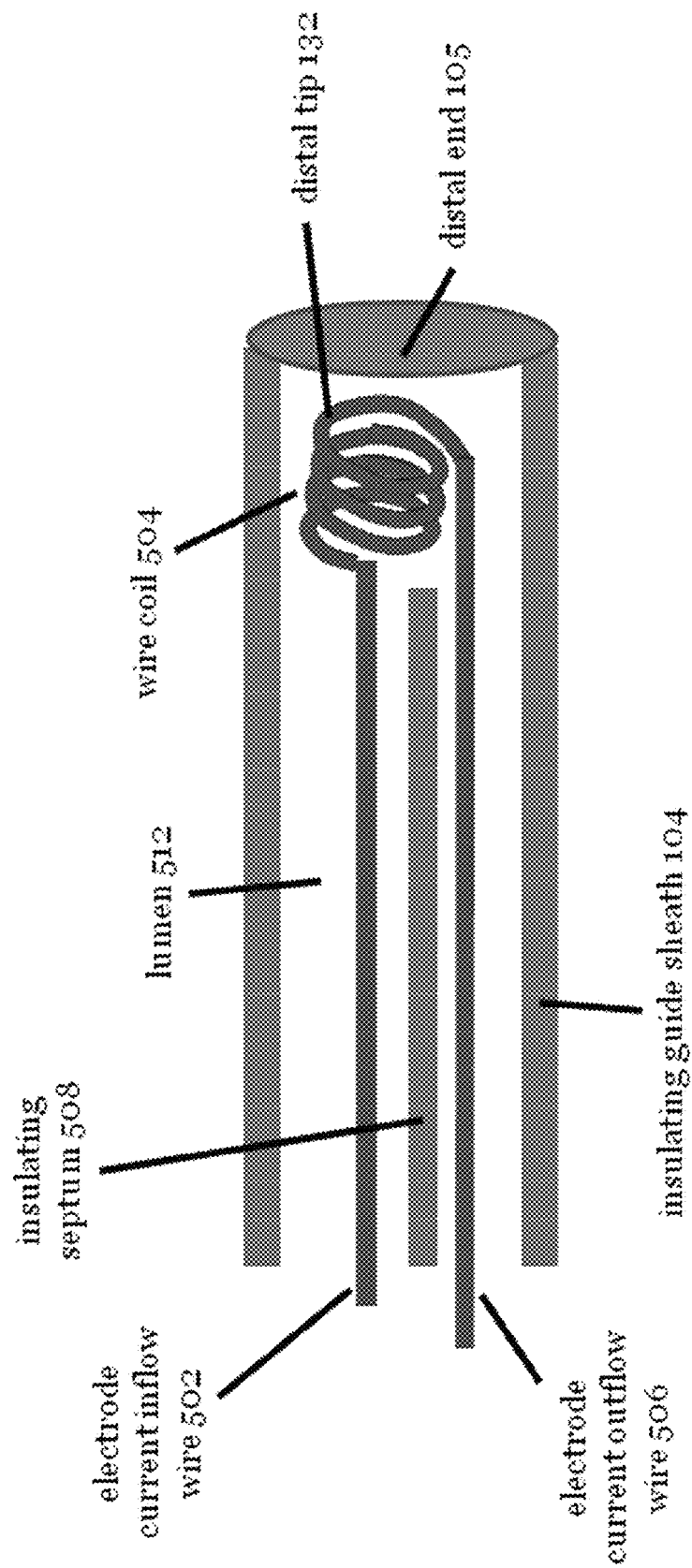

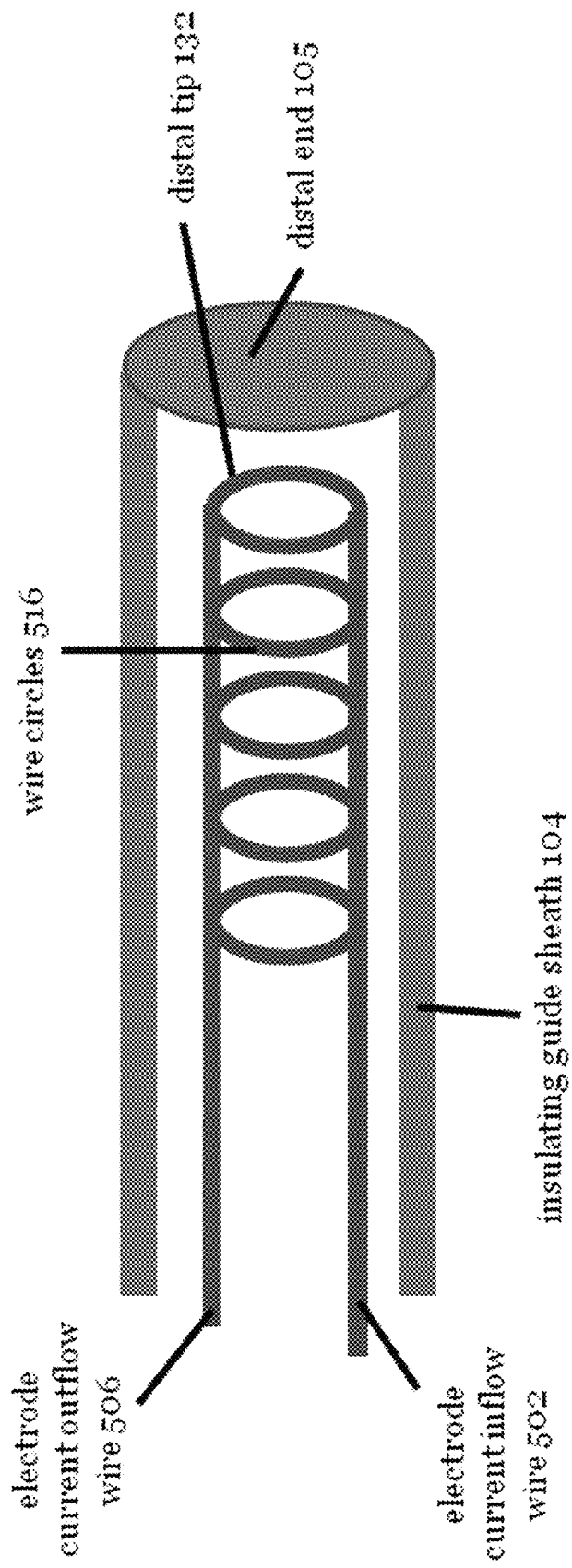

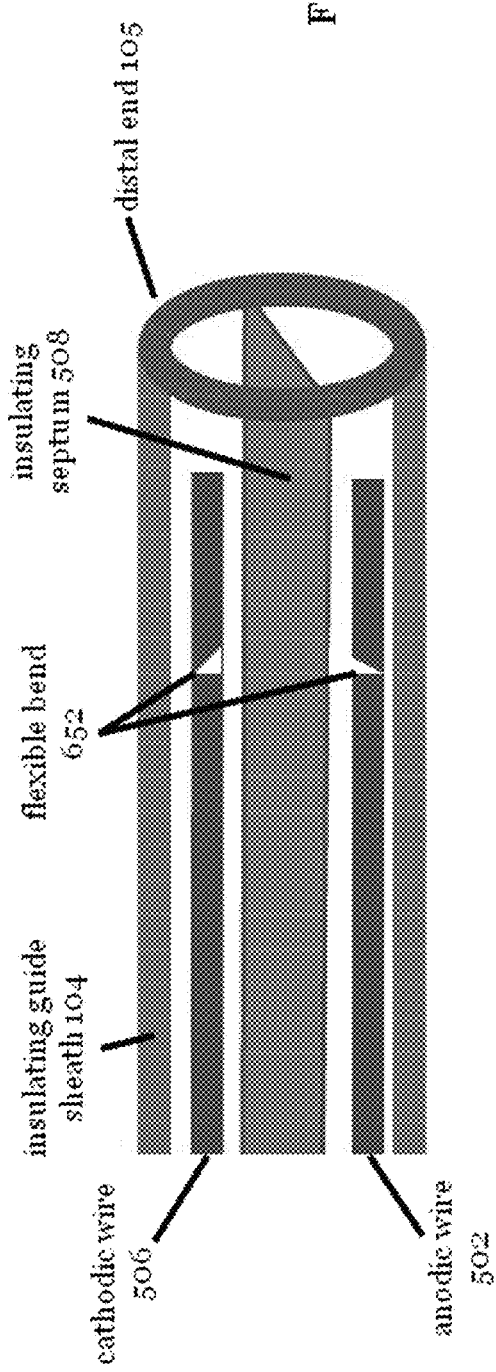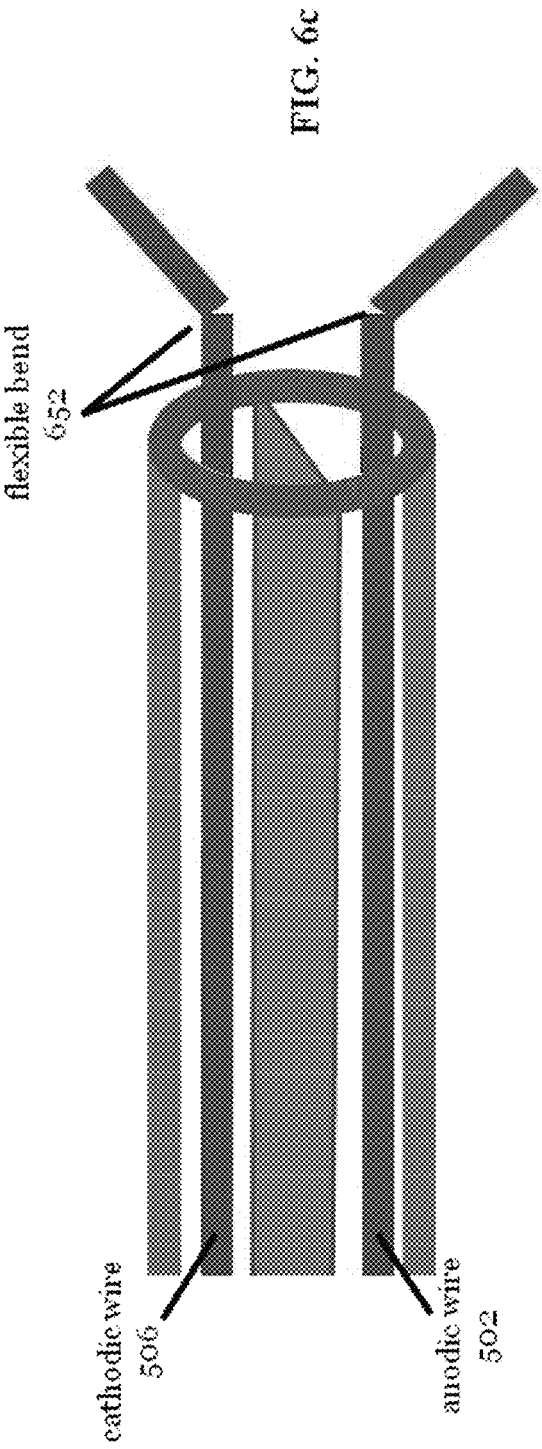

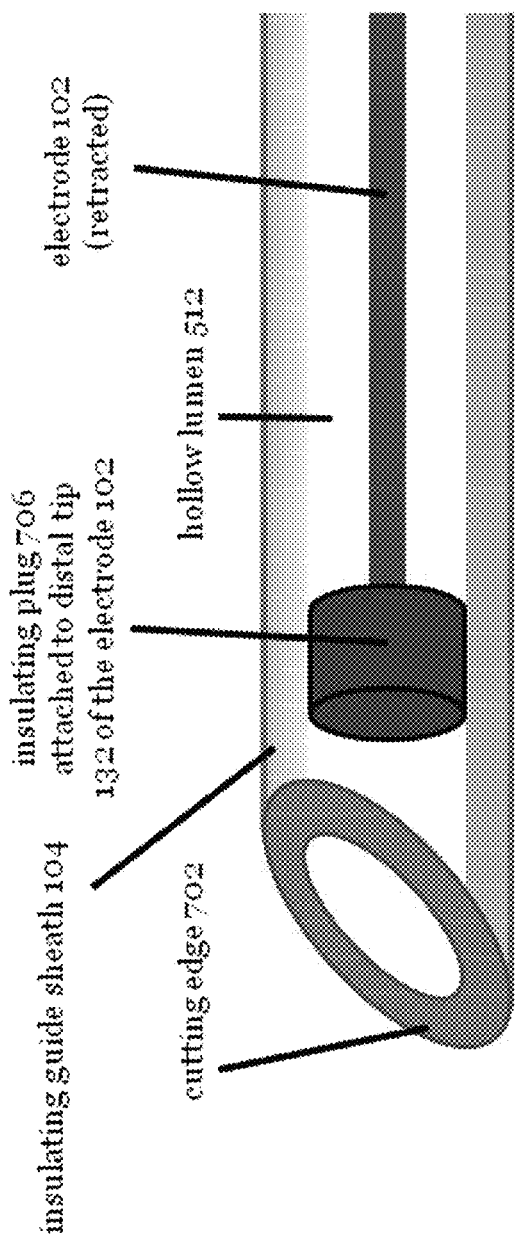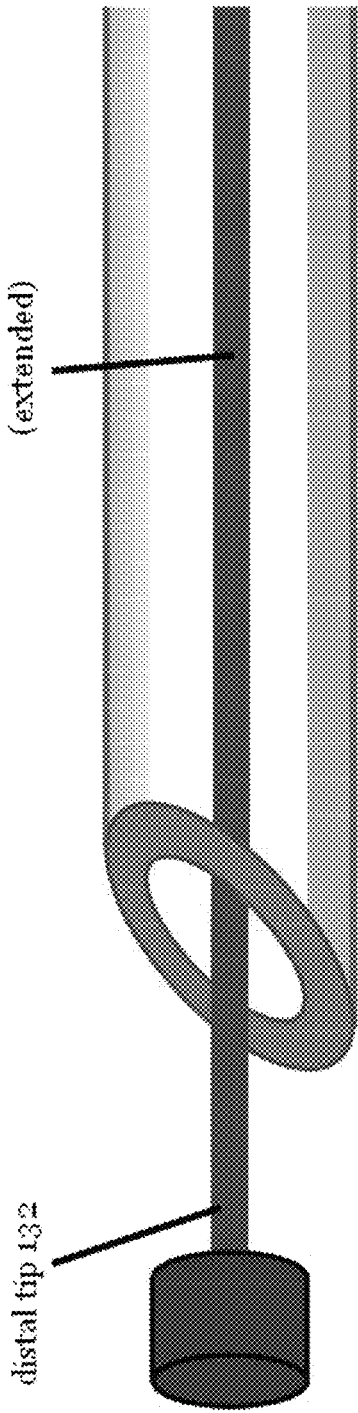
FIG. 7a
FIG. 7b

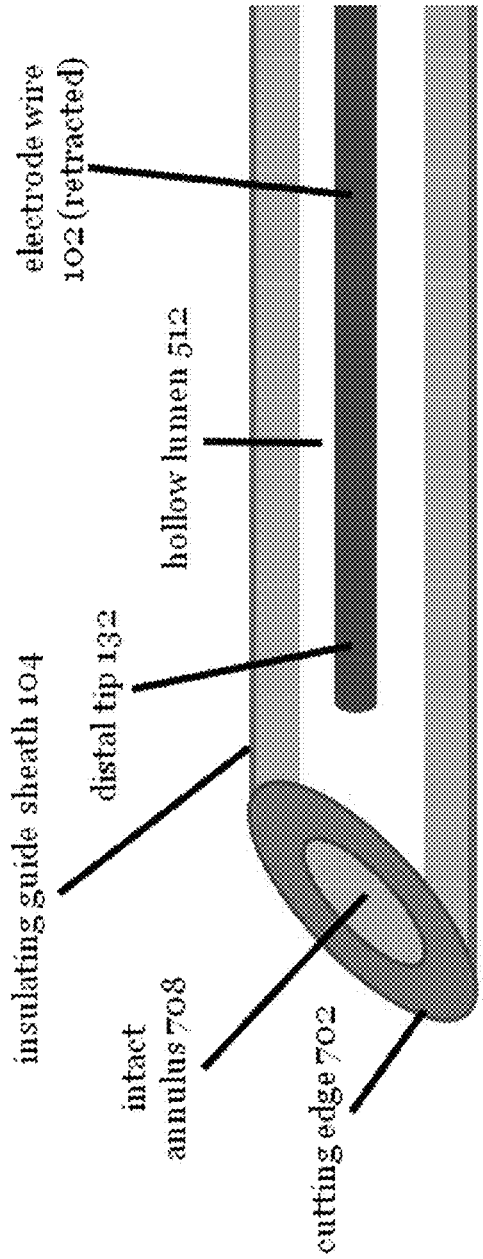
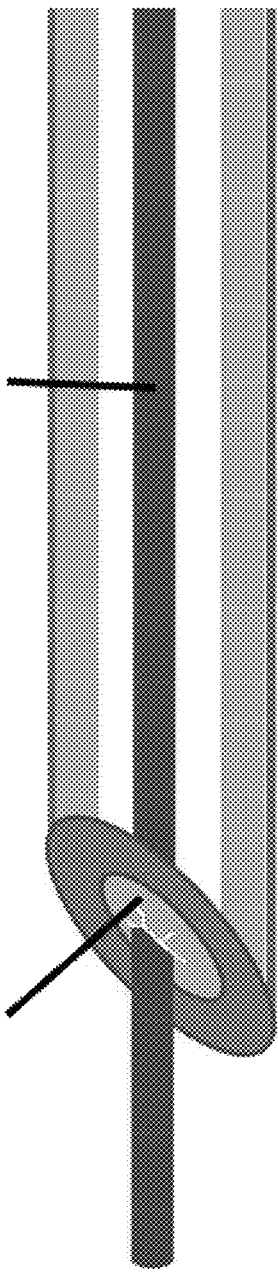
FIG. 7c
FIG. 7d

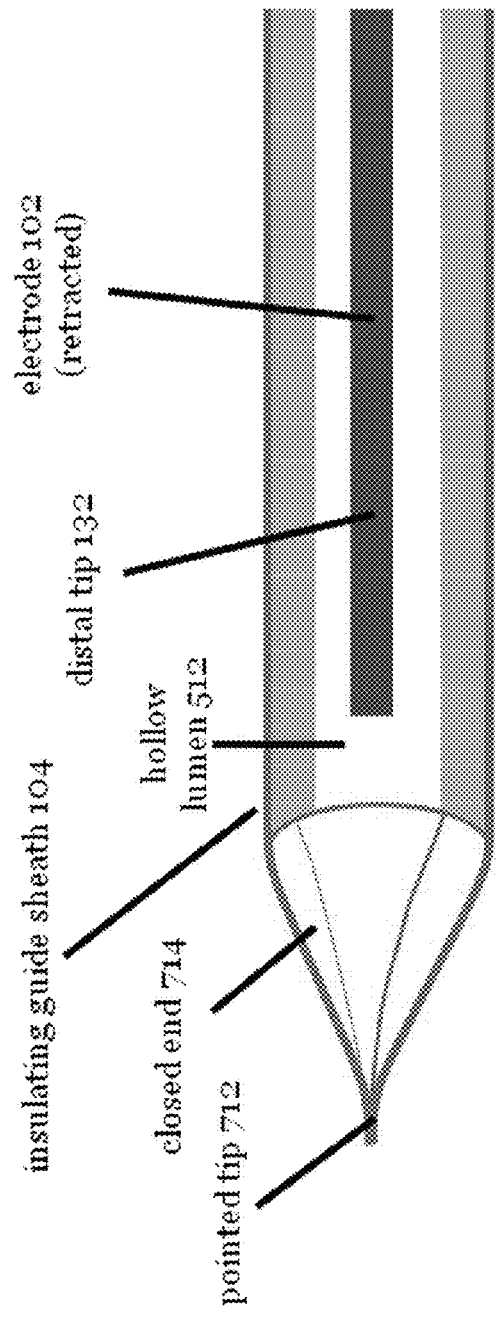
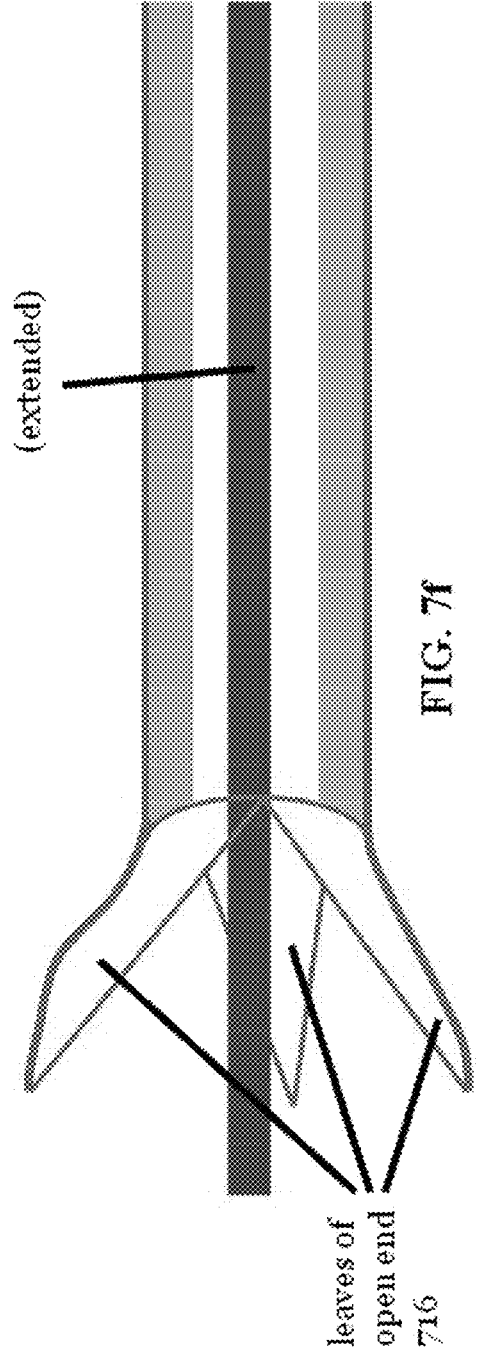

MODULATING FUNCTION OF THE FACIAL NERVE SYSTEM OR RELATED NEURAL STRUCTURES VIA THE EAR

RELATED APPLICATIONS

This application claims the benefit of U.S. Provisional Application No. 61/397,462 filed on Jun. 14, 2010, entitled "Apparatus and Means of Use for Modulating the Function of Neural Structures within and near to the Middle Ear," and of U.S. Provisional Application No. 61/330,366 filed on May 2, 2010, entitled "Apparatus and Means of Use for Modulating the Function the Tympanic Plexus, Geniculate Ganglion, Facial Nerve and/or Related Neural Structures of the Middle Ear," the entire disclosures of which are hereby incorporated by reference herein in their entireties for all purposes.

BACKGROUND OF THE INVENTION

1. Field of the Invention

The invention relates to apparatuses and methods for treatment of conditions of the cranial vasculature, and more specifically to modulating function of particular neural structures in the vicinity of the ear for treatment of stroke and other conditions.

2. Description of the Related Art

Stroke is the most common cause of physical disability and the third most common cause of death in the United States. Nearly 900,000 cases of stroke occur each year in the United States, costing $69 billion in healthcare costs. Worldwide, there are nearly 15 million cases of stroke annually; the cost of healthcare services and lost productivity on such a scale is incalculable. Most cases of stroke are caused by loss of blood flow to the brain because of occlusion of a cerebral artery or carotid artery. Cerebral artery occlusion commonly results from (1) a blood clot that is carried by the blood flow into an artery in which it becomes lodged or (2) by formation of a blood clot upon an area of atherosclerotic plaque inside the artery. Loss of blood flow by either mechanism, or by any of several less-common mechanisms, deprives areas of the brain fed by the artery of nutrients and oxygen, leading to cell death and tissue necrosis.

The emergency treatment of stroke is limited. Only one drug, the thrombolytic tissue plasminogen activator (Alteplase), has been approved for the treatment of acute stroke in the United States. Alteplase acts to dissolve blood clots such as those that occlude cerebral and carotid arteries, causing stroke. As a result, Alteplase can also cause severe intracranial hemorrhage, which is its most serious complication. In order to reduce the chance of intracranial hemorrhage, Alteplase is subject to numerous restrictions that ultimately limit its use to only about 3% of all stroke patients.

In addition to Alteplase, endovascular techniques employing intra-arterial catheters are used to treat acute stroke. Endovascular techniques, based largely on retrieval of the blood clot from the cerebral or carotid artery or else local administration of thrombolytic drugs onto the blood clot, are costly and dangerous, and their use is limited to large hospitals that have highly-trained endovascular physicians on staff. Accordingly, only several thousand stroke patients appear to be treated with endovascular techniques each year in the United States.

A possible treatment of stroke that is currently under development is electrical stimulation of the sphenopalatine ganglion. This potential treatment involves placement of a stimulator rod through the roof of the mouth (hard palate) into the vidian canal, which leads to the sphenopalatine ganglion. This device and method has a number of drawbacks. By inserting the stimulator rod through the mouth into the vidian canal, there is a risk of introducing dangerous oral bacteria into the bones of the face. In addition, the blind insertion of the stimulator rod into the confines of the vidian canal (which not only leads to the sphenopalatine ganglion but also contains the vidian artery and nerve) of the hard palate risks inducing bleeding or direct nerve injury. Furthermore, placement of the stimulator rod requires specialized training and equipment. An additional concern associated with this method is that stroke patients commonly have difficulty swallowing as part of their neurological injury. Procedures requiring implantation of foreign bodies in the mouth, as required by this method, may lead to aspiration injury in patients with airways already compromised by the neurological injury from stroke. Finally, this device and method only stimulates the sphenopalatine ganglion and its immediate connections, which in animals has a small effect on blood flow to the brain. In comparison, stimulation of the entire facial nerve—which activates the sphenopalatine ganglion as well as several other nerves and ganglia—has a much more profound effect on blood flow to the brain.

Because of the magnitude of the disease and the limited treatments for it, a significant unmet medical need exists in acute stroke. Thus, there is a need for a solution that solves the problems with current acute stroke treatments noted above, and that: (a) does not cause intracranial hemorrhage, aspiration injury, bleeding and nerve injury in the vidian canal, or facial bone infection; (b) does not require highly-trained endovascular physicians or specialized training for use; and (c) can be placed under direct visualization or else is non- or minimally-invasive.

SUMMARY OF THE INVENTION

Disclosed herein is a medical device and method that solves the above problems and that improves blood flow to the brain by causing dilation of the cerebral and carotid arteries using the body's own neural regulation of the vasculature. The invention is an apparatus and method for modulating function of particular neural structures located within the vicinity of the ear for treatment of stroke and other conditions. In one embodiment, the medical device is a stimulator that causes dilation (relaxation) of the cerebral arteries. The cerebral and carotid arteries are innervated by nerves originating in the brainstem ("cranial nerves"), one of which—the facial nerve (also known as the $7^{th}$ cranial nerve)—acts to dilate those arteries. Stimulation of the facial nerve in stroke patients may then cause dilation of the arteries supplying the brain and the head, allowing for blood flow to circumvent an obstruction and reach previously deprived brain tissue.

The device approaches the facial nerve and its branches as they pass through and near to the ear. In one embodiment, the device can be inserted into the ear canal, and it stimulates the facial nerve system without puncturing the ear drum (primary position) using stimulating energy such as an electromagnetic field. The device can also be advanced into the middle ear through an incision created in the ear drum (secondary position), and branches of the facial nerve in the middle ear can then be directly stimulated by application of electrical current. The device can be used in the emergency treatment of acute stroke or can be used as a chronically-implanted/inserted device for long-term maintenance of blood flow to the brain, e.g., in people with atherosclerotic disease of the cerebral vasculature in whom blood flow to parts of the brain is chronically compromised.

The invention can include a number of different aspects. In one aspect, the invention is an apparatus that comprises an insulating guide sheath having a proximal and a distal end. The insulating guide sheath is moveable into and out of the ear of a mammalian subject. The apparatus also includes an electrode having a proximal end and a distal tip. The electrode can be moveably disposed within the insulating guide sheath and can be placed in proximity to the tympanic membrane (ear drum) of the ear. The distal tip of the electrode can be disposed for translation within the insulating guide sheath and either (a) up to the distal end of the insulating guide sheath, but remaining inside the insulating guide sheath (e.g., when using the apparatus with the electrode positioned in the external ear) or (b) out of the distal end of the insulating guide sheath to be exposed (e.g., when using the apparatus with the electrode positioned in the middle ear). The apparatus also comprises a stimulus generator in electrical communication/direct connection with the electrode for supplying stimulus energy to the electrode for stimulating one or more components of the facial nerve system in the vicinity of the ear. In some embodiments, the stimulus generator is attached to an electrode that delivers stimulus energy, whereas in other embodiments the stimulus generator also serves as the electrode. The apparatus also includes a power source in electrical communication with the stimulus generator for providing power to the stimulus generator for supplying the stimulus energy to the electrode.

In another aspect, the invention is a method that comprises a step of moving an insulating guide sheath, having a proximal and a distal end, into the ear of a mammalian subject and a step of moving an electrode, having a proximal end and a distal tip, within the insulating guide sheath. The method also includes a step of translating the distal tip of the electrode up to the distal end of the insulating guide sheath or out of the distal end of the insulating guide sheath via the movement of the electrode to place the distal tip in proximity to the tympanic membrane of the ear. The method also includes stabilizing the insulating guide sheath to hold the insulating guide sheath in place within the ear. The method further includes supplying stimulus energy to the electrode to stimulate one or more components of the facial nerve system in the vicinity of the ear.

In a further aspect, the invention is a chronic method that comprises a step of inserting or implanting a chronic treatment device into the ear of a mammalian subject. The chronic treatment device can comprise an insulating guide sheath containing an electrode. The chronic treatment device can be inserted or implanted in proximity to the course of the facial nerve system through the temporal bone. The method also includes supplying stimulus energy to the electrode over a period of time to chronically stimulate one or more components of the facial nerve system in the vicinity of the temporal bone. The method further includes providing power via a power source for supplying the stimulus energy to the electrode.

BRIEF DESCRIPTION OF THE DRAWINGS

These and other features, aspects, and advantages of the present invention will become better understood with regard to the following description and accompanying drawings where:

FIG. 5a depicts a side, cross-sectional view of the electrode of FIG. 2 configured as a wire coil, according to an embodiment of the invention.

FIG. 5c depicts a side, cross-sectional view of the electrode of FIG. 2 configured as series of circles, according to an embodiment of the invention.

FIG. 6b depicts a side, cross-sectional view (enlargement of FIG. 6a) showing separation of the two tips of a bipolar electrode caused by flexible bends near the distal end of the wires of a bipolar electrode, with the wires retracted within the insulating guide sheath, according to an embodiment of the invention.

FIG. 6c depicts a side, cross-sectional view of the bipolar electrode of FIG. 6b, after incision of the tympanic membrane where the electrode enters the middle ear and the electrode wires are extended out of the insulating guide sheath, according to an embodiment of the invention.

FIG. 7a depicts a side, cross-sectional view of the distal tip of the apparatus having an insulating plug that is within the insulating guide sheath, according to an embodiment of the invention.

FIG. 7b depicts a side, cross-sectional view of the distal tip of the apparatus in FIG. 7a with the insulating plug after incision of the tympanic membrane, where the electrode enters the middle ear and pushes the insulating plug out, according to an embodiment of the invention.

FIG. 7c depicts a side, cross-sectional view of the distal tip of the apparatus with an annulus where the electrode is within the insulating guide sheath, according to an embodiment of the invention.

FIG. 7d depicts a side, cross-sectional view of the distal tip of the apparatus of FIG. 7c with the annulus after incision of the tympanic membrane, where the electrode enters the middle ear and perforates the annulus, according to an embodiment of the invention.

FIG. 7e depicts a side, cross-sectional view of the distal tip of the apparatus with the flower tip having the leaves closed and the electrode within the insulating guide sheath, according to an embodiment of the invention.

FIG. 7f depicts a side, cross-sectional view of the distal tip of the apparatus of FIG. 7e with a flower tip having the leaves open after lancing the tympanic membrane, where the electrode enters the middle ear and forces open the closed tip, according to an embodiment of the invention.

The skilled artisan will understand that the drawings are for illustration purposes only. The drawings are not intended to limit the scope of the present teachings in any way.

DETAILED DESCRIPTION OF THE INVENTION

Neural Structure Modulation Apparatus

The purpose of stimulation of the facial nerve system by the apparatus is to modulate the cranial blood flow. Modulation of the cranial blood flow includes increasing, decreasing, redistributing, or otherwise changing blood flow to the cerebral, carotid, and/or extracerebral arteries, including but not limited to the arteries of the brain, brainstem, face, scalp, eyes, and neck. In some embodiments, the apparatus stimulates the facial nerve system in order to increase blood flow to the brain of the subject for treatment of a stroke or to enhance delivery of a blood-borne pharmacologic agent to treat a condition of the subject. In other embodiments, blood flow to the brain or other parts of the head is decreased. As used herein, the term stroke refers to any type of stroke, and the phrase "stroke caused by atherosclerotic disease" refers specifically to stroke caused by atherosclerotic cerebral artery disease, which includes about 20% of all stroke.

Figure 1:
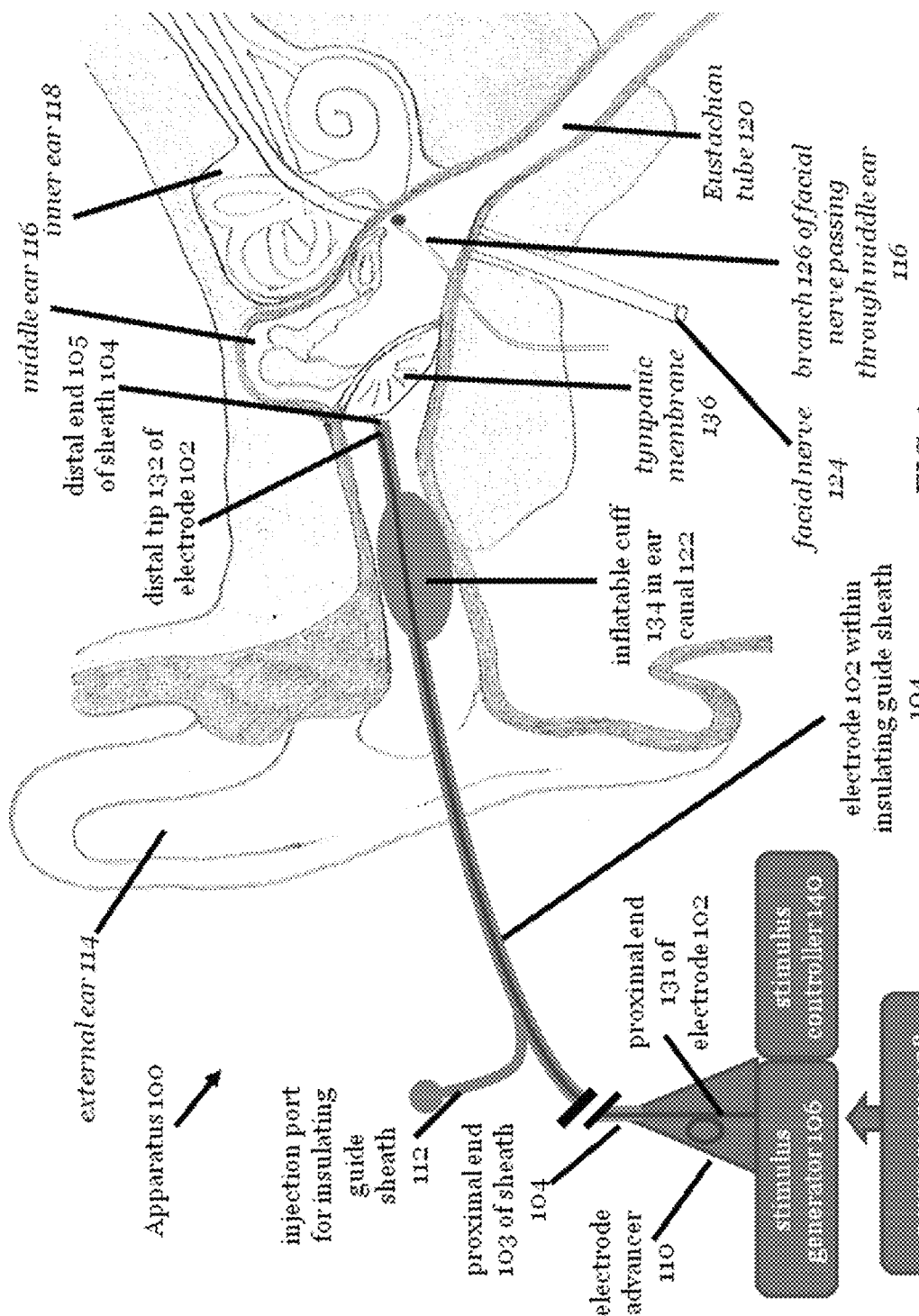
FIG. 1 depicts a side, cross-sectional view of the external and middle ear with surrounding structures, and the Figure illustrates an apparatus for modulation of the function of the facial nerve system in the primary position, according to an embodiment of the invention.

FIG. 1 depicts a side view of the apparatus 100 for treatment of conditions of the cerebral vasculature in which stimulation of part or all of the facial nerve system is accomplished through the ear, according to an embodiment of the invention. FIG. 1 illustrates various components of the ear, including the external ear 114, the middle ear 116, the inner ear 118, the tympanic membrane 136 (ear drum), and the Eustachian tube 120. As used herein, the term "ear" refers to any portion of the ear, including the external, middle, and inner ear, unless otherwise specified. FIG. 1 also illustrates certain components of the nervous system including the facial nerve 124 and a branch 126 of the facial nerve passing through the middle ear 116. The term "facial nerve system" as used herein includes, but is not limited to, the facial nerve, the geniculate ganglion, the tympanic plexus, the sphenopalatine nerves and ganglion, the petrosal nerves, the ethmoidal nerves, the palatine nerves, the vidian nerve, the communicating branches and connections of the aforementioned structures, and the communicating branches and connections between any of the aforementioned structures and the trigeminal, glossopharyngeal, or vagal nerves. These components of the facial nerve system are in the vicinity of, in proximity to, or are proximate to the ear 136. In some embodiments, the apparatus stimulates components of the facial nerve system that pass through, have a portion or branch within, or contribute to a structure within the middle ear 116. Furthermore, in some embodiments, the apparatus stimulates components of the facial nerve system that have a portion or branch within the middle ear 116 or that are immediately outside the middle ear 116. As used herein, the term "limited facial nerve system" includes the nerves listed above, but not including the sphenopalatine nerves and ganglion, the petrosal nerves and communicating branches thereof, the ethmoidal nerves and communicating branches thereof, the palatine nerves including nasopalatine nerves, the vidian nerve and communicating branches thereof, and communicating branches between any of the aforementioned structures and the trigeminal nerve system.

The apparatus 100 shown in FIG. 1 includes various components. The apparatus 100 includes an insulating guide sheath 104 having a proximal end 103 (end closest to the stimulus generator 106 and closest to the operator of the device) and a distal end 105 (end inside the ear, farthest from the operator of the device and stimulus generator). The insulating guide sheath 104 is moveable into and out of the ear (e.g., of a mammalian subject). As used herein, the term "mammalian subject" or "subject" refers to any mammal, including humans. In some embodiments, the insulating guide sheath 104 is rigid or substantially rigid (i.e., sufficiently rigid for translation into the ear but not inflexible) and is insertable into the ear via pressure or pushing of the proximal end 103 of the insulating guide sheath 104 to translate the distal tip 132 into the ear. The apparatus 100 also includes an electrode 102 that also has a proximal end 131 and a distal tip 132. As used herein, the term "electrode" includes a stimulation device that provides stimulation, such as stimulation or stimulus energy in the form of an electric current or in the form of an electromagnetic or magnetic field. In some embodiments, the electrode 102 is housed within the insulating guide sheath 104. In some embodiments, the electrode 102 is a straight wire or plurality of wires. In some embodiments, the electrode 102 is a coiled wire or wire formed into a non-linear shape. In some embodiments, the electrode 102 and insulating guide sheath 104 together form a stimulator. In further embodiments, the distal tip 132 of the electrode 102 is detachable from the electrode 102 and is replaceable with a plurality of different distal tips that are attachable to the electrode 102. Thus, the apparatus 100 can be reused with new/clean distal tips 132 if desired or if the type of stimulation (e.g., electrical, electromagnetic) delivered by the electrode 102 is to be changed.

In the apparatus 100 shown in FIG. 1, the insulating guide sheath 104 is moveably disposed within the ear and the electrode 102 is moveably disposed within the insulating guide sheath 104. In some embodiments, the electrode 102 and insulating guide sheath 104 are advanced together into the ear. In other embodiments, the insulating guide sheath 104 is advanced into the ear first, and the electrode 102 is advanced within the insulating guide sheath 104 and into the ear. In some embodiments, the distal tip 132 of the electrode 102 can be advanced up to the distal end 105 of the insulating guide sheath 104. In some embodiments, the distal tip 132 is further advanced out of the distal end 105 of the insulating guide sheath 104 so that the distal tip 132 is exposed.

Figure 3:
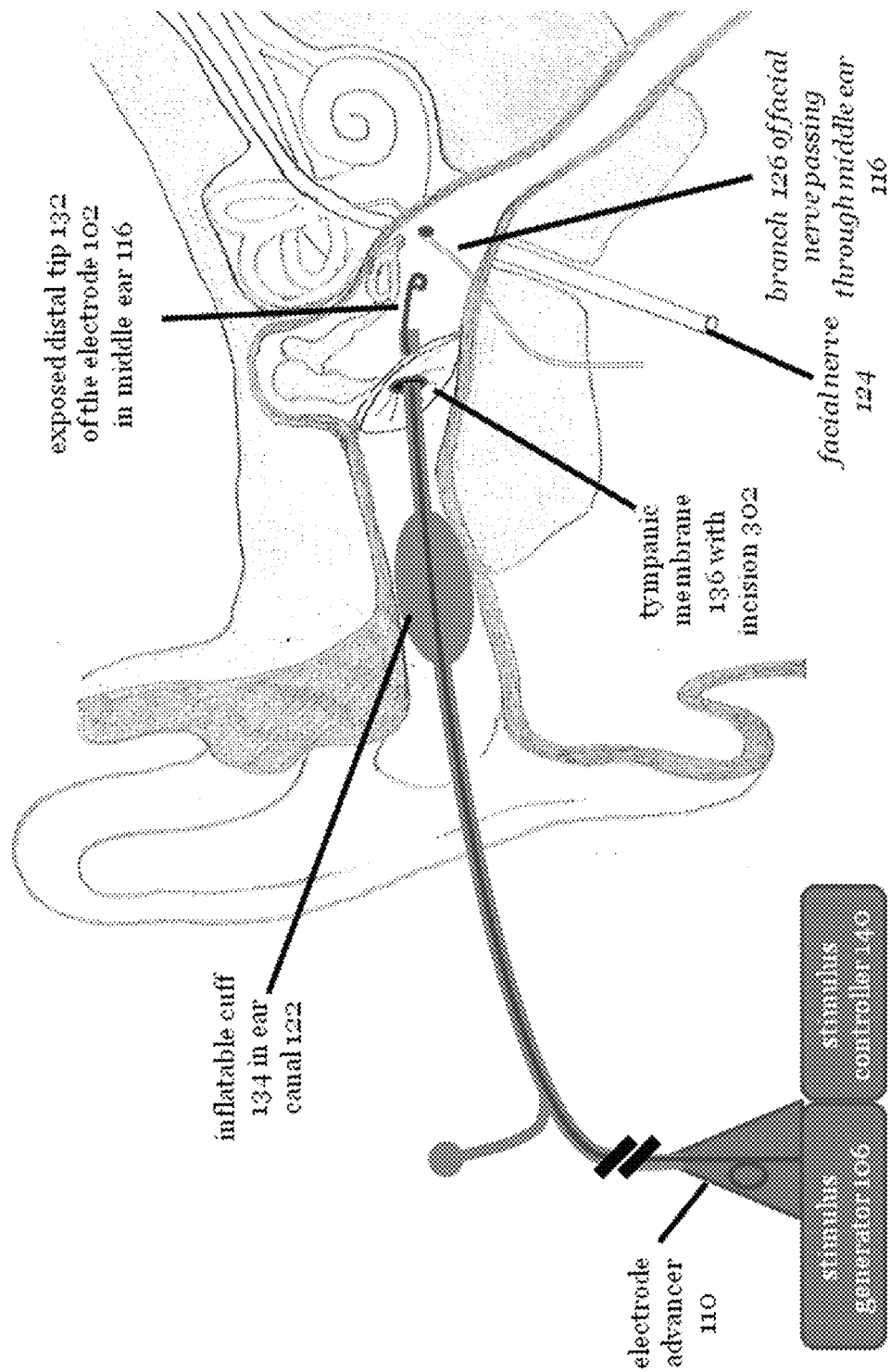
FIG. 3 depicts a side, cross-sectional view of the external and middle ear with surrounding structures, and the Figure illustrates the apparatus for modulation of the function of the facial nerve system in the secondary position, according to an embodiment of the invention.

There are two positions for the apparatus 100, as follows: the primary position and the secondary position. FIG. 1 illustrates the primary position and FIG. 3 illustrates the secondary position. For the primary position, the electrode 102 and the insulating guide sheath 104 are advanced into the ear canal 122 near to the tympanic membrane 136, and the electrode 102 is disposed to remain inside the insulating guide sheath 104 (or the electrode tip can be translated out of the insulating guide sheath 104 and exposed, if desired). In the primary position, the electrode 102 remains external to the tympanic membrane 136, and so remains within the ear canal 122. For the secondary position, the distal tip 132 of the electrode 102 is disposed for translation out of the distal end 105 of the insulating guide sheath 104 to be exposed (or it can be kept within the insulating guide sheath 104 if desired) and placed in proximity to a tympanic membrane 136 of the ear. Thus, the insulating guide sheath 104 and electrode 102 are passed into the middle ear 116, and so are positioned internal to the tympanic membrane 136. In this situation, the tympanic membrane 136 is incised or punctured to insert the insulating guide sheath 104 and electrode 102 through the incised tympanic membrane 136 and into the middle ear 116. The tympanic membrane 136 can be incised in various ways. In one embodiment, the distal end 105 of the insulating guide sheath 104 is sharp, and this sharpened distal tip can be pushed through the tympanic membrane 136 to create an opening to reach the middle ear 116. In other embodiments, a separate instrument can be used to make an incision in the tympanic membrane 136. According to some embodiments, both the insulating guide sheath 104 and electrode 102 are inserted into the middle ear 116. According to other embodiments, only the electrode 102 is inserted into the middle ear 116 while the insulating guide sheath 104 remains in the ear canal 122. In some embodiments, the insulating guide sheath 104 is between 6 cm and 12 cm in length in order to allow access to the middle ear 116 through the ear canal 122.

Once the insulating guide sheath 104 is in place within the ear, it can be fixed into position to prevent unintended movement. In one embodiment, the insulating guide sheath 104 is fixed into position by inflation of an inflatable cuff 134 on the insulating guide sheath 104 in the ear canal 122, though other stabilization mechanisms can also be used, including stabilization with an ear piece or clip fixed to the external ear 114 (not shown). In some embodiments, the inflatable cuff 134 is attached to the outer wall of the insulating guide sheath 104 and the inflatable cuff 134 is configured to fit against a surface of the ear for holding the insulating guide sheath 104 in place within the ear. The inflatable cuff 134 can be used to fix the insulating guide sheath 104 into the primary position or the secondary position.

A stimulus generator 106 can be in electrical communication with the electrode in 102 various ways. For example, the stimulus generator 106 can be directly connected to the electrode 102 (e.g., connected via one or more wires or other connectors), or indirectly connected to or in communication with the electrode 102. A power source 108 can be placed in electrical communication with the stimulus generator 106 for providing power to the stimulus generator 106 for supplying the stimulus energy to the electrode 102. The power source 108 can also be directly or indirectly connected to the stimulus generator 106. For example, the power source 108 can connect to the stimulus generator 106 via one or more wires or other connectors, but the power source 108 can also indirectly connect to or be in communication with the stimulus generator 106, such as via a wireless communication method. In some embodiments, the power source 108 provides power to the stimulus generator 106, and the stimulus generator 106 provides stimulus energy to the electrode 102 that then provides stimulation to one or more aspects of the facial nerve system.

In addition, the apparatus 100 can include an electrode advancer 110 to which the proximal end 131 of the electrode 102 is attached or associated. The electrode advancer 110 can include an advancement mechanism for advancing the electrode 102 within the insulating guide sheath 104 and/or for advancing the insulating guide sheath 104 into the ear.

While FIGS. 1-4 show the insulating guide sheath 104 and electrode 102 being inserted into the ear via the ear canal 122, these components can be also configured for insertion into the middle ear 116 via a Eustachian tube 120 of the subject. Various disease processes in the ear canal or upon the tympanic membrane may impair access of medical devices through the ear canal. To overcome limited access through the ear canal 122, an apparatus capable of accessing the middle ear through the Eustachian tube 120 can be employed. The Eustachian tube 120 connects the middle ear 116 with the nasopharynx, allowing for pressure equilibration between the middle ear 116 and the external environment and for drainage from the middle ear 116 to enter the throat. The insulating guide sheath 104 and electrode 102 can be inserted into the Eustachian tube 120 without direct visualization through transnasal positioning, under direct visualization transnasally, or under direct visualization transorally. The insulating guide sheath 104 and electrode 102 can then be advanced along the Eustachian tube 120 and into the middle ear 116. In some embodiments, the insulating guide sheath 104 is between 20 cm and 30 cm in length in order to allow access to the middle ear 116 through the Eustachian tube 120. Once placed in the middle ear 116 through the Eustachian tube 120, the apparatus 100 can then be used as explained above, i.e., to apply stimulus energy to one or more components of the facial nerve system for stroke treatment, etc.

Filling of the ear canal, or of the middle ear, with electrically-conductive material, gel, or solution may be used to achieve the desired result of the invention. Thus, in some embodiments, the apparatus 100 further includes an injection port 112 connected to the insulating guide sheath 104. The injection port 112 can be a tube or other structure attached to an opening in the wall of the insulating guide sheath 104. The injection port 112 can include an opening on one end into which the user can insert a material, gel, or solution. The injection port 112 is used for injecting into the insulating guide sheath 104 a material, gel, or solution to facilitate treatment of the subject. The material, gel, or solution is contained within the insulating guide sheath 104 following injection, and in some embodiments, some or all of the material, gel, or solution is transferred through the insulating guide sheath 104 for release from the distal end 105 of the insulating guide sheath 104. A variety of different materials, gels, or solutions can be placed into the lumen of the insulating guide sheath through the injection port 112. For example, an electrically-conductive gel or solution can be injected into an ear canal 122 or middle ear 116 of the subject to increase conductivity. As another example, an anesthetic or other pharmacological agent used to eliminate an unwanted response of tissue local to the electrode 102 can be injected into an ear canal 122 or middle ear 116. The pharmacological agent can also be added to the conductive material, gel, or solution. In some embodiments, the injection port 112 connects into a single lumen within the insulating guide sheath 104. In other embodiments, the injection port 112 connects into one of a plurality of lumens within the insulating guide sheath 104.

In some embodiments, the apparatus 100 further includes a stimulus controller 140 attached to the stimulus generator 106 for adjusting the stimulus energy applied to the electrode 102. The stimulus controller 140 can include a user interface by which the operator of the apparatus can provide instructions to or otherwise interact with the apparatus 100. The stimulus controller 140 can allow the operator to control the strength, frequency, and/or other parameters of the stimulus energy. For example, the controller 140 can include particular controls (e.g., knobs, digital settings, etc.) for increasing or decreasing the strength of the current and controlling various other factors in the operation of the apparatus 100. Where the apparatus 100 is connectable to a computer or other machinery, the operator may also be able to interact with and control the apparatus 100 via the interface of the computer, including tracking the subject's vital signs, responses to the stimulus energy over time, and so forth.

The stimulus controller 140 can further be used to adjust the stimulus energy for various purposes. For example, the stimulus energy can be adjusted based on one or more physiological or pathophysiological responses of the subject to the stimulus energy (e.g., taste sensation; audition; lacrimation; nasal drainage; nasal congestion; salivation; sound sensitivity; face, head, or hand movements; speech production or arrest; sensation of body movement; eye movements; cranial blood flow; direct or indirect activity of a nerve; and severity of neurological dysfunction of the subject). For example, if the subject exhibits certain eye movements, the operator can observe this and respond to this by changing the stimulus energy or certain other parameters associated with the stimulus energy. As another example, the apparatus 100 itself can determine or interact with other instrumentation to detect certain physiological or pathophysiological responses of the subject to the stimulus energy, and the apparatus 100 can automatically adjust the stimulus energy in response. As a further example, the stimulus energy can be adjusted to increase or otherwise control blood flow to the brain of the subject as either the direct treatment of a disease process or else to facilitate the delivery of blood-borne pharmacologic agents as the treatment of a disease process.

Figure 2:
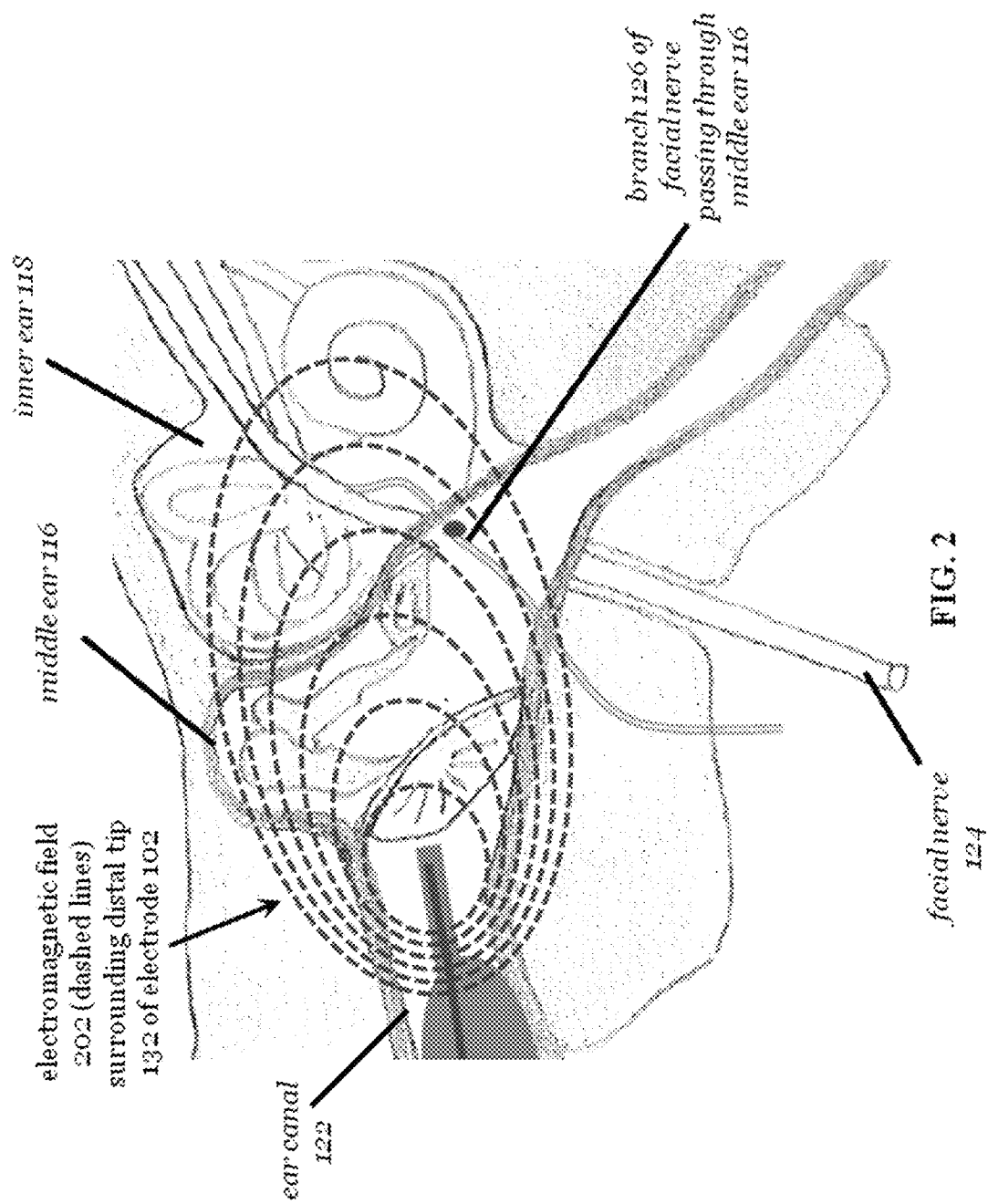
FIG. 2 depicts a side, cross-sectional view of the ear (enlargement of FIG. 1) including stimulation by the apparatus in the primary position, according to an embodiment of the invention.

The apparatus 100 also includes a stimulus generator 106 in electrical communication with the electrode 102 for supplying stimulus energy to the electrode 102 for stimulating one or more components of the facial nerve system. In some embodiments, the stimulus energy is electrical current applied through the electrode 102 that creates an electromagnetic field 202 that is of sufficient strength to stimulate one or more components of the facial nerve system located in the vicinity of the ear. FIG. 2 illustrates the insulating guide sheath 104 and electrode 102 in the primary position, and further illustrates application of the stimulus energy, according to an embodiment of the invention. In this embodiment, the stimulus energy is electrical current applied to the electrode 102 in order to create an electromagnetic field 202 that is of sufficient strength to stimulate one or more components of the facial nerve system located in, or in the vicinity of, the middle ear 116. Thus, the electromagnetic field 202 is used to stimulate the facial nerve system with the electrode 102 being in the ear canal 122, on the external side of the tympanic membrane 136. In some embodiments, the electromagnetic field 202 is defined by various combinations of the following parameters: a stimulation frequency ranging from 0.01 to 100 Hz; a field strength of 0.01 to 5.0 Tesla; a biphasic or oscillatory waveform. In some embodiments, the electromagnetic field 202 is applied intermittently or periodically. In some embodiments, stimulation with certain parameters reduces or redirects blood flow to the brain.

In some embodiments, failure of the electrode to achieve the desired result when used in the primary position is followed by advancement of the electrode 102 into the middle ear 116 to put the apparatus 100 into the secondary position. In this embodiment, the tympanic membrane 136 is incised using the sharpened distal end 105 of the insulating guide sheath 104 or other mechanism for allowing the insulating guide sheath 104 and/or electrode 102 to enter the middle ear 116. The insulating guide sheath 104 can be fixed into place in the ear canal 122 or advanced through the incision in the tympanic membrane 136 and then fixed into place, and the electrode 102 can be advanced past the distal end 105 of the insulating guide sheath 104 into the middle ear 116. Electrical current can then be applied through the exposed tip of the electrode 102 in order to stimulate one or more components of the facial nerve system. This is referred to as the secondary position. In the secondary position, one or more components of the facial nerve present within the middle ear 116 can be subjected to stimulation by direct exposure to electrical current. In some embodiments, the electrode comprises a cathode and an anode. In one embodiment, the closest distance between the cathode and the anode is greater than the closest distance between any portion of the cathode and any portion of a tympanic plexus, facial nerve, or other neural structure of the middle ear. In some embodiments, the electrode is monopolar and a ground wire is applied to an external ear or other part of the head.

FIG. 3 illustrates the apparatus 100 in the secondary position, according to an embodiment of the invention. The insulating guide sheath 104 has been fixed into place by the inflatable cuff 134 in the ear canal 122. The insulating guide sheath 104 has been used to incise the tympanic membrane 136. The incision 302 (e.g., puncture hole) is illustrated in FIG. 3 and the insulating guide sheath 104 and electrode 102 have been advanced through the incision 302 into the middle ear 116. The electrode 102 has further been advanced within the insulating guide sheath 104 so that the distal tip 132 of the electrode 102 is exposed. In some embodiments, the distal tip 132 of the electrode 102 is positioned near a branch 126 of the facial nerve 124 that is passing through middle ear 116.

Figure 4:
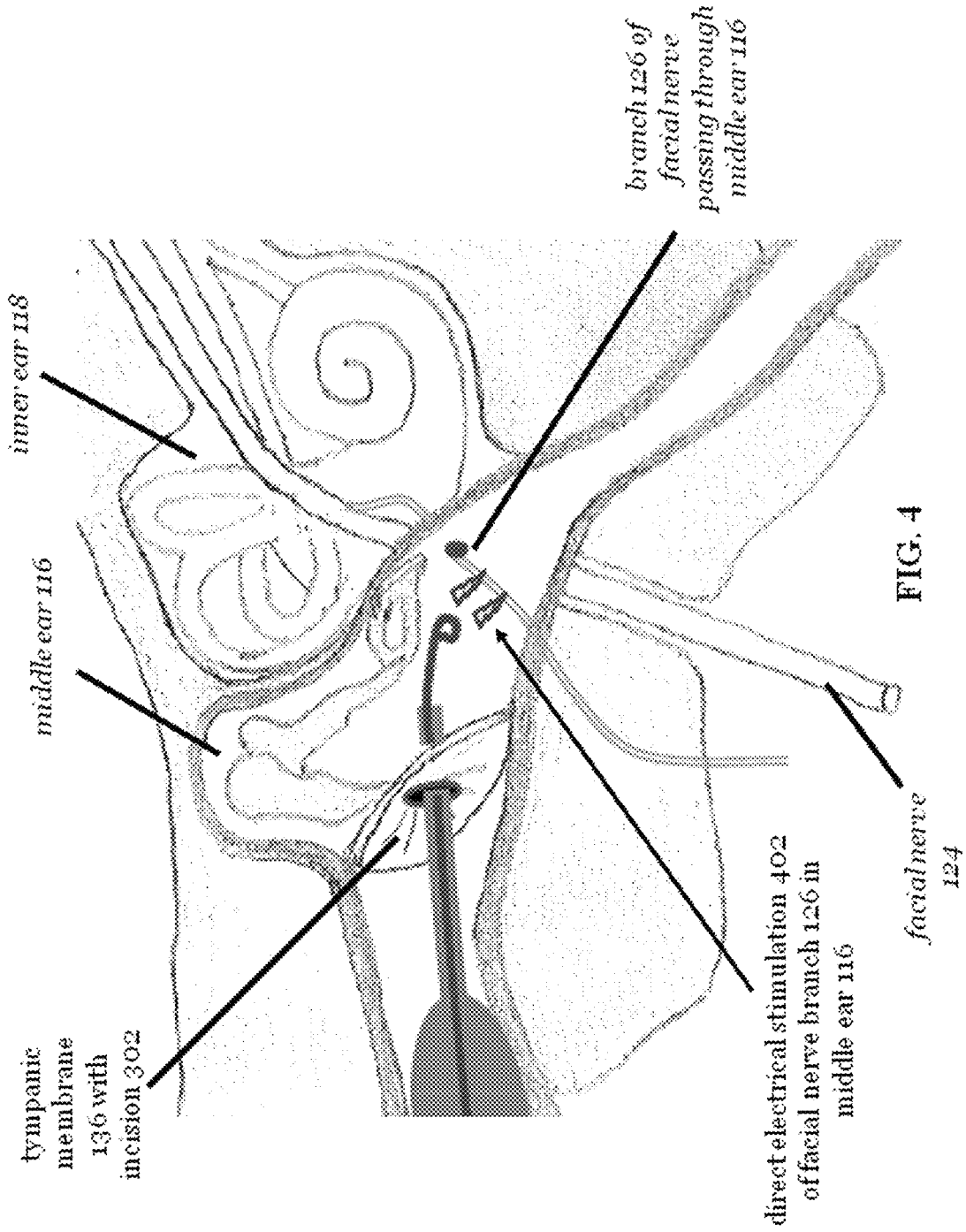
FIG. 4 depicts a side, cross-sectional view of the ear (enlargement of FIG. 3) including stimulation by the apparatus in the secondary position, according to an embodiment of the invention.

FIG. 4 illustrates the apparatus 100 in the secondary position with the stimulus energy being applied to the electrode 102. FIG. 4 illustrates direct electrical stimulation 402 of a facial nerve branch 126 in the middle ear 116. In some embodiments, the electrode is retained within the insulating guide sheath 104 and application of the electrical current to the electrode 102 creates an electromagnetic field 202 that penetrates various tissues in order to stimulate components of the facial nerve system. In some embodiments, the electrical stimulation 402 is defined by various combinations of the following parameters: a stimulation frequency ranging from 0.1 to 100 Hz; a current of 0.1 to 5.0 mA; a biphasic waveform with or without a delay between the phases. In some embodiments, the electrical stimulation 402 is provided intermittently or periodically. In some embodiments, stimulation with certain parameters decreases or shunts off blood flow to the brain.

Figure 5B:
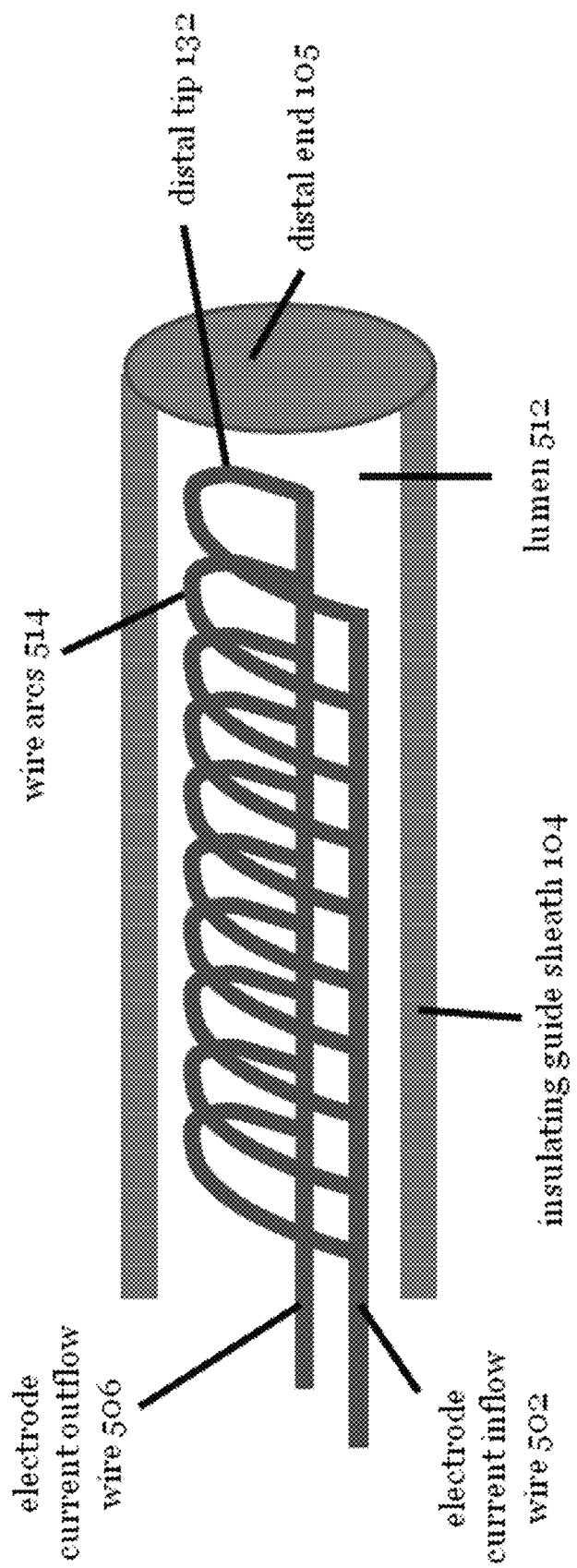
FIG. 5b depicts a side, cross-sectional view of the electrode of FIG. 2 configured as a series of arcs, according to an embodiment of the invention.

FIGS. 5a-c illustrate the distal tip 132 of the apparatus 100 used in the primary position, and further illustrate examples of various configurations of the distal tip 132 of the electrode 102 suitable for generating an electromagnetic field 202. FIG. 5a illustrates the distal tip 132 of the electrode 102 configured as a wire coil 504 with repeating loops that connects at one end to the electrode current inflow wire 502 and at the other end to the electrode current outflow wire 506, according to an embodiment of the invention. The electrode current inflow wire 502 and electrode current outflow wire 506 are separated by an insulating septum 508 or other means of insulation within the lumen 512 of the insulating guide sheath 104. In some embodiments, and as shown in FIG. 5a, the wire coil 504 is positioned near the distal end 105 of the insulating guide sheath 104 with its axis largely parallel to the direction of the electrode wires. In other embodiments, the wire coil 504 is positioned within the lumen 512 of the insulating guide sheath 104 with its axis largely perpendicular to, or significantly angled away from, the direction of the electrode wires (not shown). In some embodiments, the wire coil 504 is tapered as is a cone. In some embodiments, the wire coil 504 has an outer diameter of less than 6 mm, an inner diameter of at least 2 mm, and a length of 10-30 mm. In some embodiments, the wire coil is coiled into 5-25 layers with 50-250 turns per layer.

FIG. 5b illustrates the distal tip 132 of an electrode 102 configured as one or more wire arcs 514, according to an embodiment of the invention. As shown in FIG. 5b, in some embodiments, a series of arcs are placed at the distal tip 132 of the electrode 102 between the electrode current inflow wire 502 and the electrode current outflow wire 506, so as to form electrical connections between the electrode current inflow wire 502 and the electrode current outflow wire 506. In some embodiments of the invention, the arcs are inclined from the plane formed by the electrode current inflow wire 502 and the electrode current outflow wire 506 within the lumen 512 of the insulating guide sheath 104. In some embodiments, the distance between the electrode current inflow wire 502 and the electrode current outflow wire 506 is minimal, thereby pulling the wire arcs 514 into substantially noose-like shapes (not shown). In some embodiments, 4-50 wire arcs 514 are employed.

FIG. 5c illustrates the distal tip 132 of an electrode 102 configured as one or more wire circles 516, according to an embodiment of the invention. In some embodiments, the wire circles 516 are placed between the electrode current inflow wire 502 and the electrode current outflow wire 506 so that the electrode current inflow wire 502 and the electrode current outflow wire 506 connect to the wire circles 516 at a single point. In some embodiments, the wire circles 516 are placed between the electrode current inflow wire 502 and the electrode current outflow wire 506 so that their planes are not perpendicular to the direction of the electrode current inflow wire 502 or the electrode current outflow wire 506. In some embodiments, the wire circles 516 are distorted so that their shape is substantially oval. In some embodiments, the wire circles 516 are distorted so that all the points along the wire do not lie within a single plane (not shown).

Referring to FIGS. 5a-c, the wire and insulating guide sheath 104 can be constructed in various ways. In some embodiments, the wire comprising the shapes illustrated in FIGS. 5a-c is between 0.06-0.60 mm in diameter. In some embodiments of apparatus 100, the insulating guide sheath 104 is composed of poly(4,4'-oxydiphenylene-pyromellitimide) (KAPTON®), polyimide, or polytetrafluoroethylene (PTFE or TEFLON®). In some embodiments, the insulating guide sheath 104 is prepared with a conformal coating.

Everything described above including the various embodiments of the distal tip of the electrode described in FIGS. 5a-c can apply to the remaining designs, such as FIGS. 6-14. For example, the description of the sizes, shapes, designs, and materials used in the construction of the components of FIGS. 5a-c can apply to the apparatus designs of FIGS. 6-14. However, for ease of presentation and clarity, these details are not repeated again below for each of FIGS. 6-14.

Figure 6A:
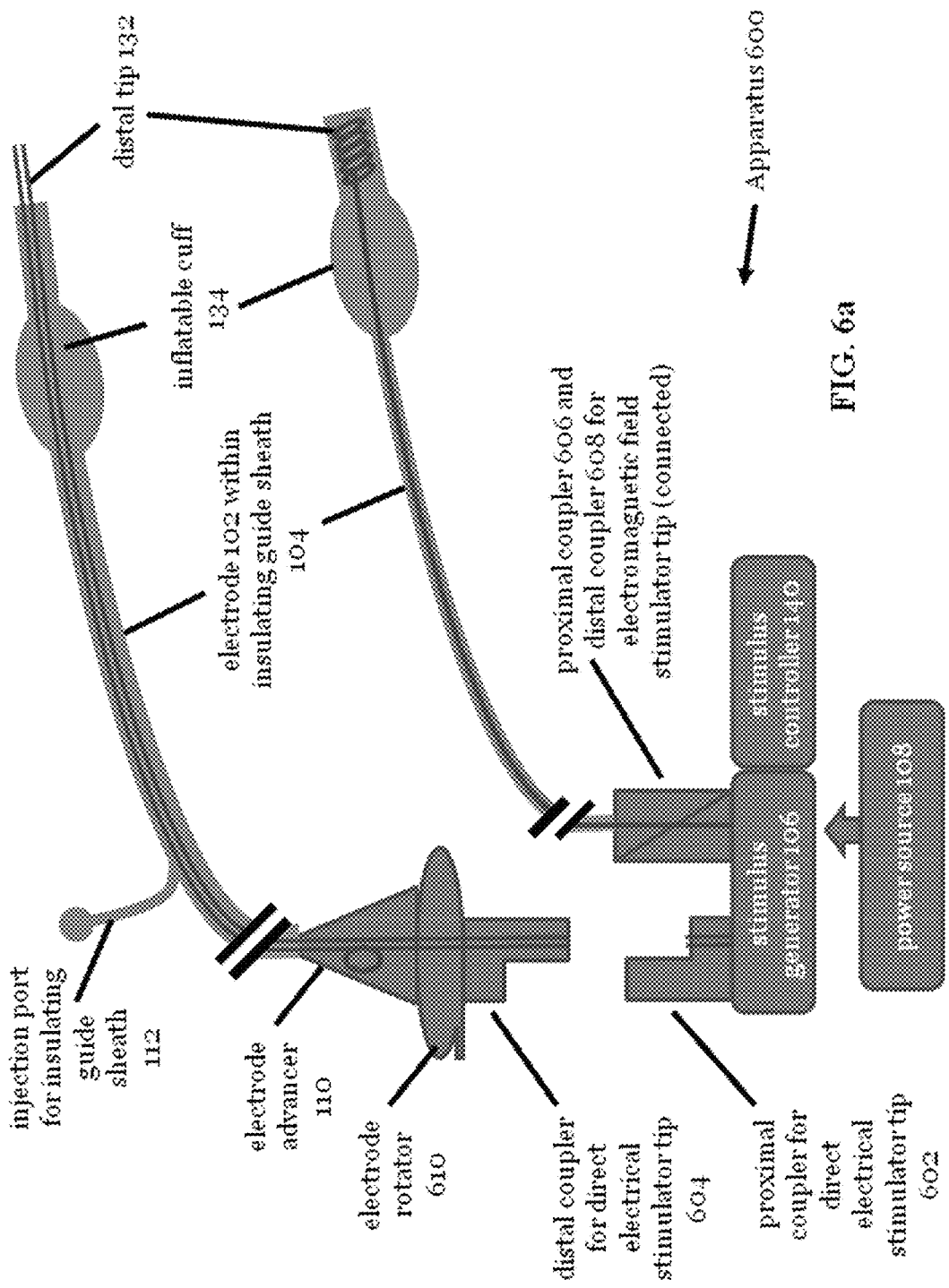
FIG. 6a depicts a side, cross-sectional view of the apparatus demonstrating multiple interchangeable electrodes and the manner in which they connect to the stimulus generator.

FIG. 6a illustrates an apparatus 600 that allows for exchange of electrodes for use in the primary and secondary positions, according to an embodiment of the invention. For use of an electromagnetic field stimulator in the primary position, a junction is formed by the union of a distal coupler 608 and proximal coupler 606, in which the distal coupler 608 is in electrical communication with the electrode 102 at the proximal end 103 of the insulating guide sheath 104, and in which the proximal coupler 606 is in communication with the stimulus generator 106. Connection of the proximal coupler 606 and the distal coupler 608 places the electrode in electrical continuity with the stimulus generator 106 allowing stimuli to be delivered through the electrode that then generates an electromagnetic field 202. For use in the secondary position, the electromagnetic field stimulator described above is removed by disconnection of the distal coupler 608 from the proximal coupler 606 specific for that stimulator type. Then, a stimulator type appropriate for the secondary position is attached, e.g., through a distinct junction. In this example, an electrode capable of delivering direct electrical stimulation through its uninsulated distal tip 132 is attached by means of a distal coupler 604 at the proximal end 131 of the electrode to a proximal coupler 602 on the stimulus generator 106, wherein the distal coupler 604 and the proximal coupler 602 are specific for this type of electrode and are not typically used with other electrode types (e.g., those that generate electromagnetic fields). Connection of the proximal coupler 602 and the distal coupler 604 places the electrode in electrical continuity with the stimulus generator 106, allowing stimuli to be delivered through the electrode and released from the distal tip 132 as direct electrical current or voltage.

In some embodiments, attachment of one electrode type by means of connection of the proximal coupler 602,606 to the distal coupler 604,608 prohibits the simultaneous attachment of another electrode type to the apparatus. In some embodiments, attachment of an electrode type by means of a proximal coupler 602,606 and a distal coupler 604,608 determines, adjusts, or limits the power delivered by the power source 108.

In some embodiments, a bipolar electrode is used to deliver stimulation in the secondary position of the device, as shown in FIG. 6a. In order to optimally orient the bipolar electrode within the middle ear 116 space, an electrode rotator 610 is positioned at or near the proximal end 131 of the electrode for use in the secondary position. The electrode rotator 610 is used to rotate one pole of the bipolar electrode around the second pole, or else to rotate both poles around a common axis, or to otherwise adjust the positioning of the electrode. In some embodiments, rotation of one or more of the electrode poles is achieved by rotating the insulating guide sheath 104 that houses the poles of the bipolar electrode. An electrode advancer 110 can also be attached at or near the proximal end of the bipolar electrode such that one or both poles of the bipolar electrode can be advanced from, or retracted into, the insulating guide sheath 104.

As shown in FIG. 6b, in some embodiments, a bipolar electrode is formed by a cathodic wire 506 and an anodic wire 502 that are housed within separate lumens within the insulating guide sheath 104. In some embodiments, separate lumens are formed by an insulating septum 508 or other such division. In some embodiments, flexible bends 652 are placed in the electrode wire near the distal ends of the cathodic wire 626 and anodic wire 622. As shown in FIG. 6c, when the electrode wires are advanced out of the distal end 105, the flexible bends 652 spread the tips of the electrode wires apart by a predetermined distance. In other embodiments, separate lumens within the insulating guide sheath 104 open at different positions along the length of the insulating guide sheath 104 so that a fixed distance exists between the cathodic wire 626 and anodic wire 622 once the wires are advanced out of the insulating guide sheath 104 (not shown).

The wire or wires of the electrode for use in the secondary position to deliver stimulation in the middle ear 116 is/are formed or constructed in various ways. In some embodiments, the wire or wires is/are formed from stainless steel, platinum, silver alloy, gold alloy, or nitinol. In some embodiments, the wire or wires of the electrode may be square or in a strip shape. In some embodiments, the wire or wires of the electrode may be capped at their distal ends so as to be non-traumatic once extended from the insulating guide sheath 104.

FIGS. 7a and 7b illustrate the distal end 105 of the insulating guide sheath 104, according to an embodiment of the invention. FIG. 7a illustrates the electrode 102 within the hollow lumen 512 of the insulating guide sheath 104 for use in the primary position. The distal end 105 of the insulating guide sheath 104 includes a cutting edge 702 that is used to incise or create an opening in the tympanic membrane 136 through which the insulating guide sheath 104 and electrode 102 can be passed. FIG. 7a further shows an insulating plug 706 attached to the distal tip 132 of the electrode 102. The insulating plug 706 protects and insulates the distal tip 132 of the electrode 102. FIG. 7a shows the electrode retracted within the hollow lumen 512 of the insulating guide sheath 104. FIG. 7b shows the distal tip 132 of the electrode 102 extended from the hollow lumen 512 of the insulating guide sheath 104. After incision of the tympanic membrane 136, the electrode 102 pushes the insulating plug 706 out of the insulating guide sheath 104 and enters the middle ear 116, achieving the secondary position.

FIGS. 7c and 7d illustrate the distal end 105 of the insulating guide sheath 104, according to an embodiment of the invention. FIG. 7c illustrates the electrode 102 within the hollow lumen 512 of the insulating guide sheath 104 for use in the primary position. Like the embodiment of FIGS. 7a and 7b, FIGS. 7c and 7d illustrate an embodiment in which the distal end 105 of the insulating guide sheath 104 includes a cutting edge 702 that is used to incise the tympanic membrane 136 through which the insulating guide sheath 104 and electrode 102 can then be passed. FIG. 7c further shows an intact annulus 708 and FIG. 7d shows a perforated annulus 710. FIG. 7c shows the electrode retracted within the hollow lumen 512 of the insulating guide sheath 104. FIG. 7d shows the distal tip 132 of the electrode 102 extended from the hollow lumen 512 of the insulating guide sheath 104 through the annulus, causing perforation of the annulus. In other words, after incision of the tympanic membrane 136, the electrode 102 perforates the annulus to insert the distal tip 132 of the electrode 102 into the middle ear 116, achieving the secondary position.

FIGS. 7e and 7f illustrate the distal end 105 of the insulating guide sheath 104, according to an embodiment of the invention. FIG. 7e illustrates the electrode 102 within the hollow lumen 512 of the insulating guide sheath 104 for use in the primary position. FIGS. 7e and 7f illustrate an embodiment in which the insulating guide sheath 104 includes a pointed tip 712 that is used to incise the tympanic membrane 136 through which the insulating guide sheath 104 and electrode 102 can be passed. FIG. 7e shows the electrode 102 retracted within the hollow lumen 512 of the insulating guide sheath 104 and the closed end 714 of the insulating guide sheath 104. FIG. 7f shows the open end 716 of the insulating guide sheath 104. The distal end 105 of the insulating guide sheath 104 in this embodiment includes three leaves (though more or fewer leaves can be included) that are moved apart to open the closed end 714. Once open, the distal tip 132 of the electrode 102 is extended from the hollow lumen 512 of the insulating guide sheath 104. Thus, after lancing the tympanic membrane 136, the electrode 102 forces open the closed end 714 of the insulating guide sheath 104 and enters the middle ear 116, achieving the secondary position.

Figure 8:
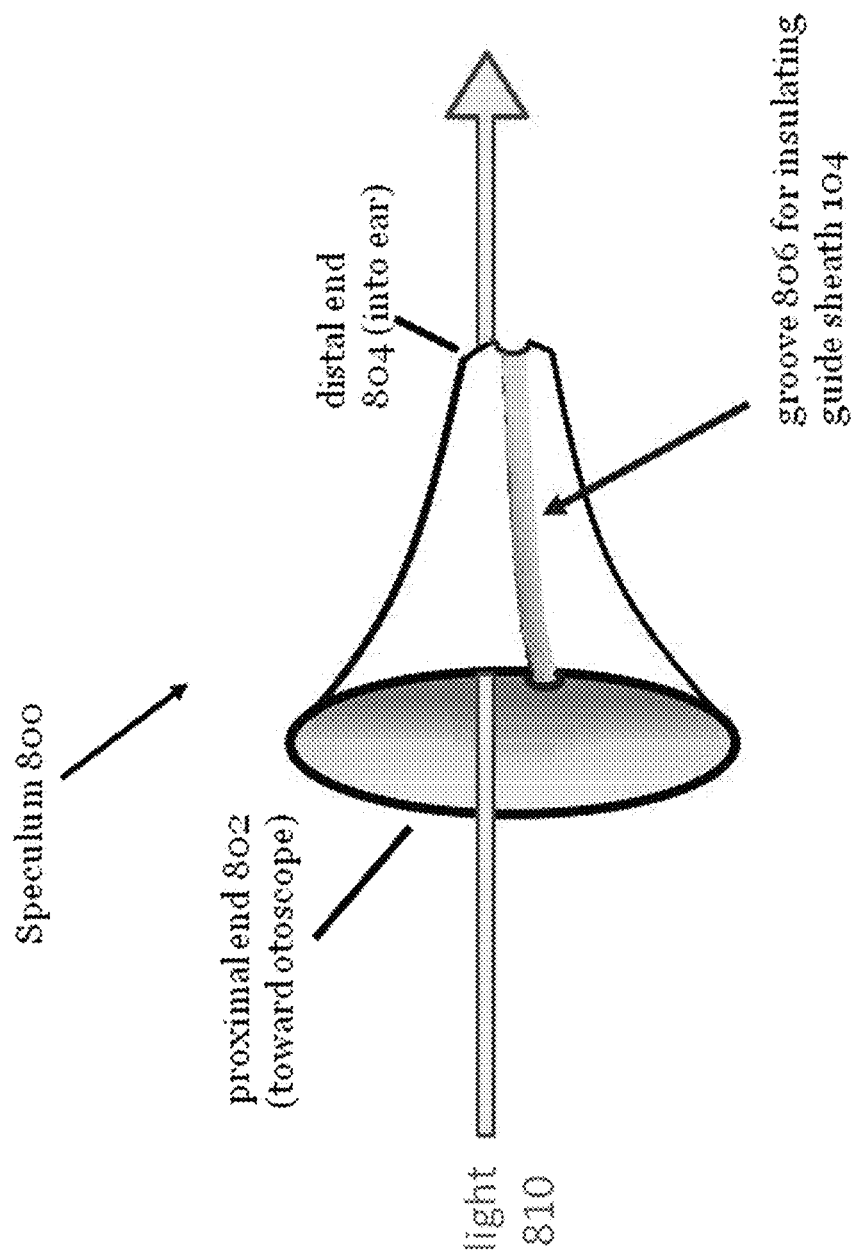
FIG. 8 depicts a side view of a speculum for use with the apparatus, according to an embodiment of the invention.

FIG. 8 illustrates a speculum 800 for use with the apparatus 100, according to an embodiment of the invention. Placement of the insulating guide sheath 104 and electrode 102 in the ear canal 122 or in the middle ear 116 may require a specialized otoscope speculum 800 that will allow for direct visualization of anatomical structures. The ear speculum 800 can be composed of a hollow, largely conical structure with openings at its proximal end 802 and distal end 804. The speculum 800 can also be modified with a groove 806 or other peripheral channel along its lateral length, where the groove 806 or other peripheral channel is of sufficient size to accommodate the guide sheath 104. In this embodiment, the groove 806 allows for lateral passage of the insulating guide sheath 104 and for manipulation of the insulating guide sheath 104 and electrode 102. The groove 806 can be on the outside of the speculum 800 or can be inside the speculum 800. The groove 806 can be open along its length so that the speculum 800 can be separated from the insulating guide sheath 104 once the speculum 800 is removed from the ear (e.g., after successful positioning of the insulating guide sheath 104). The groove 806 can also be closed along its length to hold the insulating guide sheath 104 in place during placement of the insulating guide sheath 104 in the ear. Where the groove 806 is closed, it can include a latch or other mechanism for opening the groove 806 to release the insulating guide sheath 104.

The distal end 804 of the speculum 800 is placed into the ear facing into the tympanic membrane 136 for direct visualization inside the ear canal 122. The proximal end 802 of the speculum 800 faces toward an operator and may be connected to an otoscope which will allow the visualization. Light 810 can be shone through the opening in the speculum 800 and into the ear canal 122 to view the inside of the ear. The opening of the proximal end 802 of the speculum 800 is significantly larger than the opening of the distal end 804 of the speculum 800, and the proximal end 802 can be attached to an ordinary otoscope from which light is projected through the hollow lumen of the speculum 800. During placement of the apparatus 100 in its primary or secondary positions, the distal end 804 of the speculum 800 can be inserted into the ear canal 122 of the subject, allowing direct visualization of the ear canal 122 and tympanic membrane 136. The insulating guide sheath 104 and electrode 102 can then be advanced down the length of the groove 806 in the speculum 800 and manipulated into proper position.

Figure 9:
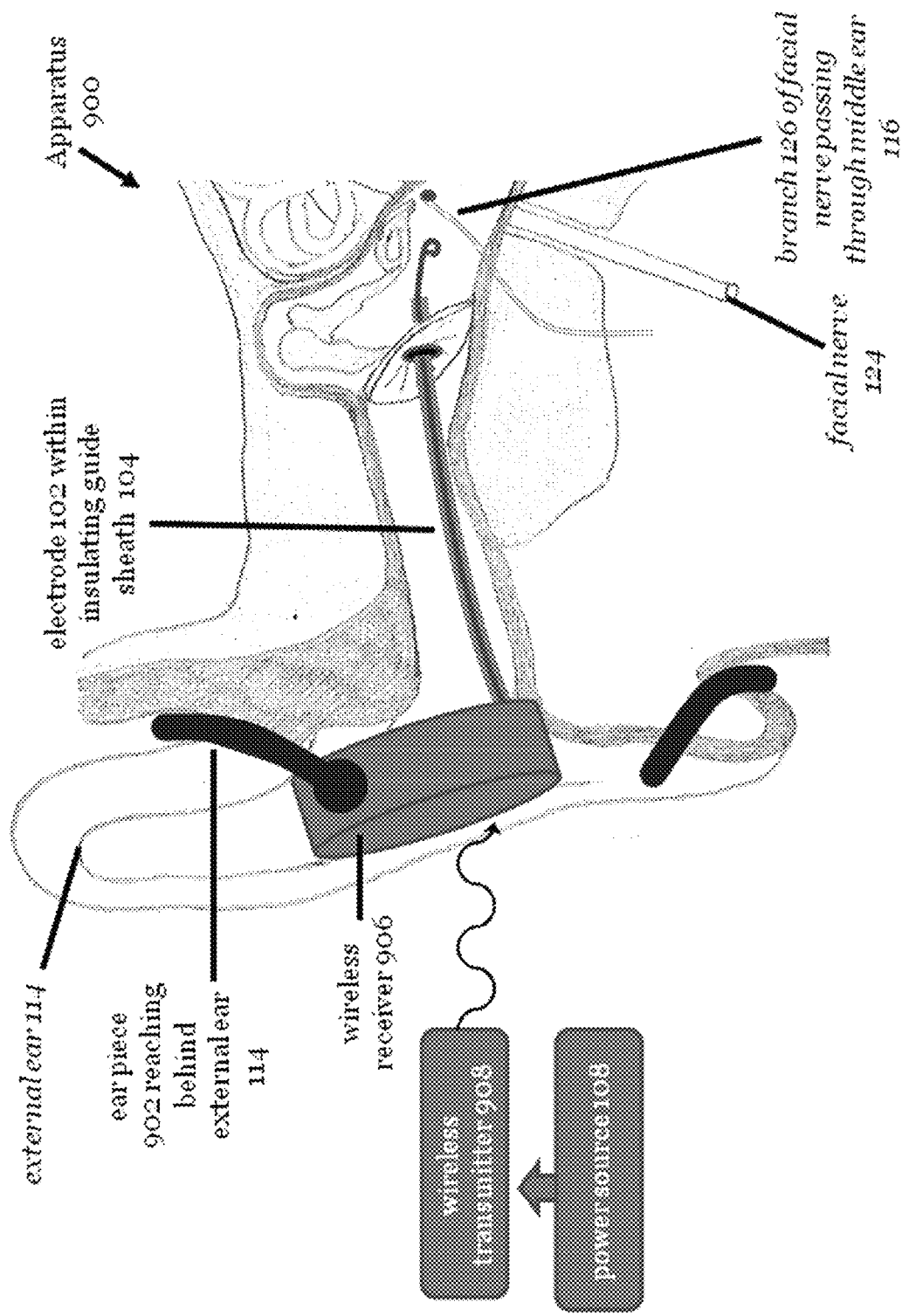
FIG. 9 depicts a side, cross-sectional view of an ear piece of the apparatus with a stimulus generator placed on the external ear and an insulating guide sheath containing the electrode that are insertable into the ear canal, where the apparatus includes a wireless transmitter and receiver, according to an embodiment of the invention.

FIG. 9 illustrates a side view of apparatus 900 with the stimulus generator 106 resting against the external ear 114, according to an embodiment of the invention. In this embodiment, the stimulus generator 106 is an outer covering, plug, or other design that sits outside the ear canal 122. In some embodiments, the stimulus generator 106 is shaped as a ring or a hook that sits upon the pinna, concha, scapha, tragus, or antitragus of the external ear (not shown).

In FIG. 9, the stimulus generator 106 is comprised of a wireless transmitter 908 and a wireless receiver 906. The electrode 102 and the insulating guide sheath 104 are connected to the wireless receiver 906, and the wireless receiver 906 sits against the external ear 114 in a manner that places the electrode 102 and insulating guide sheath 104 inside the ear canal 122, bringing the distal tip 132 of the electrode 102 into proximity to the tympanic membrane 136. Proximity to the tympanic membrane 136 is defined in relation to either the internal face of the tympanic membrane (observed from the position in the middle ear 116) or the external face of the tympanic membrane (observed from the position of the ear canal 122).

As shown in FIG. 9, the distal tip 132 of the electrode 102 is placed through an incision 302 in the tympanic membrane 136 within the middle ear 132, achieving the secondary position. In other embodiments, the distal tip 132 of the electrode 102 is placed near the external face of the tympanic membrane 136 within the ear canal 122, achieving the primary position (not shown). The wireless receiver 906 is held in place on the external ear 114 by an ear piece 902 that rests against the head, in this embodiment behind the external ear 114. A variety of other ear piece designs can be used for holding the wireless receiver 906 in place as well. In this embodiment, the ear piece 902 is designed in FIG. 9 to wrap around the back side of the ear and under the ear lobe. The apparatus 900 further includes a wireless transmitter 908 that can be separate and unattached from the body of the subject, or that can be attached to the body somewhere on the body or in clothing on the body (e.g., in a pocket, attached to a belt, worn around the neck, etc.). The wireless transmitter 908 is directly or indirectly in communication with a power source 108 that provides power to the wireless transmitter 908. In some embodiments, one or more wires electrically couple the power source 108 to the wireless transmitter 908.

The wireless transmitter 908 can communicate with the wireless receiver 906 on the distal ear piece 904 to generate stimulus energy for the electrode 102. The wireless receiver 906 and the wireless transmitter 908 can be electromagnetically or inductively coupled.

The apparatus 900 of FIG. 9 can be a chronic treatment device or can be an acute treatment device. For acute treatment of a stroke, the apparatus 900 can be placed on the subject's ear, and can deliver stimulus energy as desired by a physician or other operator. The stimulus generator 106 can be attached to a stimulus controller 140 that allows a physician or other operator to control when the energy is delivered, the intensity of the energy, etc. For chronic treatment of a stroke, the apparatus 900 can be worn as a chronic treatment device that is worn regularly by the subject. It can be worn all the time, at certain times of day, or whenever prescribed. The apparatus 900 can thus chronically stimulate and modulate one or more components of the facial nerve system in the vicinity of the ear. In another embodiment, one or more components of the chronic treatment apparatus are shaped to fit into an ear canal of the subject or against the external ear (e.g., as shown in FIG. 9 or another design to be worn externally by the subject). In this embodiment, the components are on an external side of the tympanic membrane for chronically stimulating and modulating one or more components of the facial nerve system in the vicinity of the ear.

Figure 10:
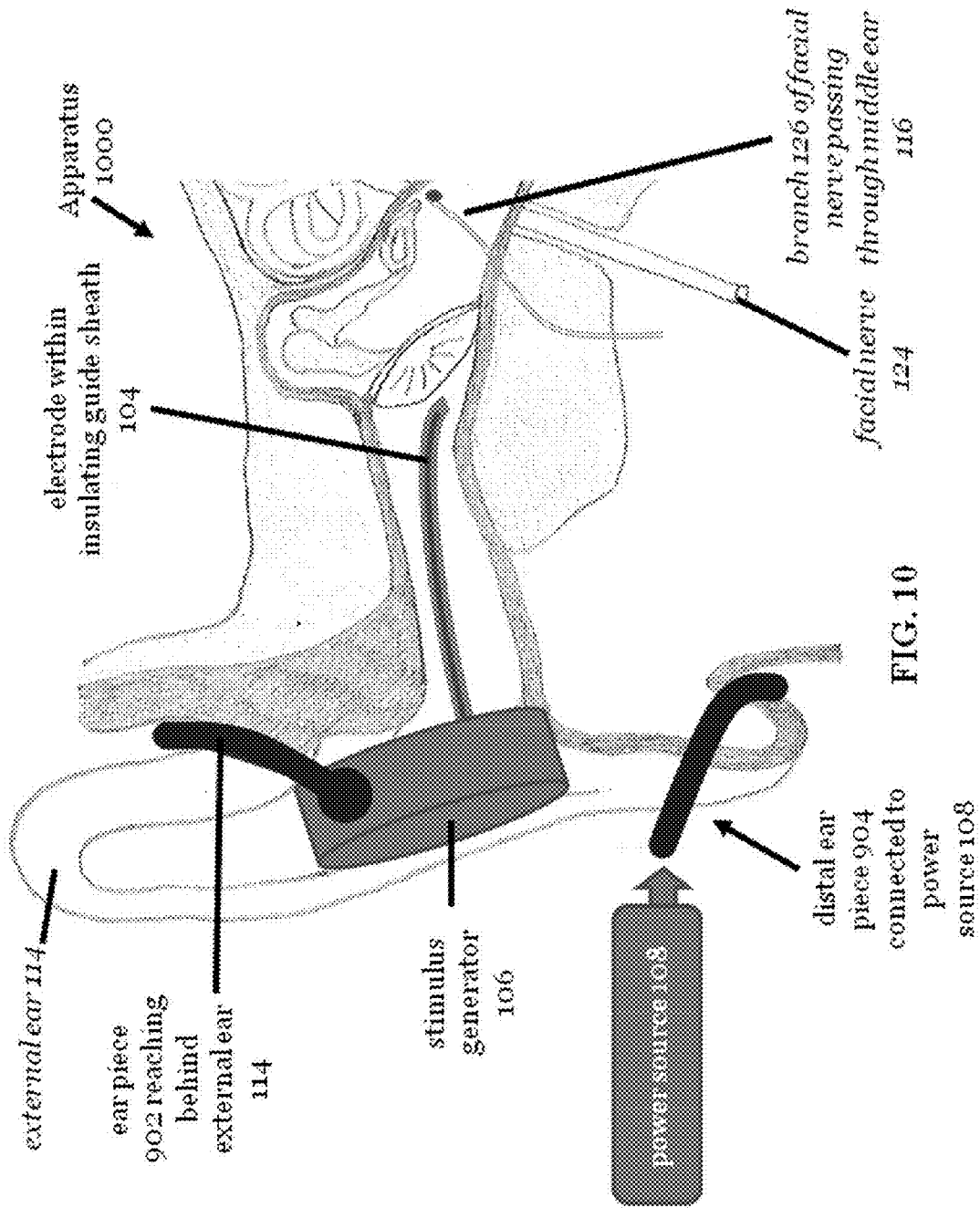
FIG. 10 depicts a side, cross-sectional view of an ear piece of the apparatus with a stimulus generator placed on the external ear and an insulating guide sheath containing the electrode that are insertable into the ear canal, where the ear piece connects to the power source, according to an embodiment of the invention.

FIG. 10 illustrates a side view of apparatus 1000 with the stimulus generator 106 resting against the external ear 114, according to an embodiment of the invention. The design is similar to that of FIG. 9, but in this case the power source 108 directly connects to the distal ear piece 904. There is no wireless transmitter or receiver in this embodiment, therefore the stimulus generator 106 is represented as a single object that received power from the power source 108 through the ear piece 902. The distal tip 132 of the electrode 102 can be placed in proximity to the tympanic membrane 136, achieving either the primary or secondary position as needed.

Figure 11A:
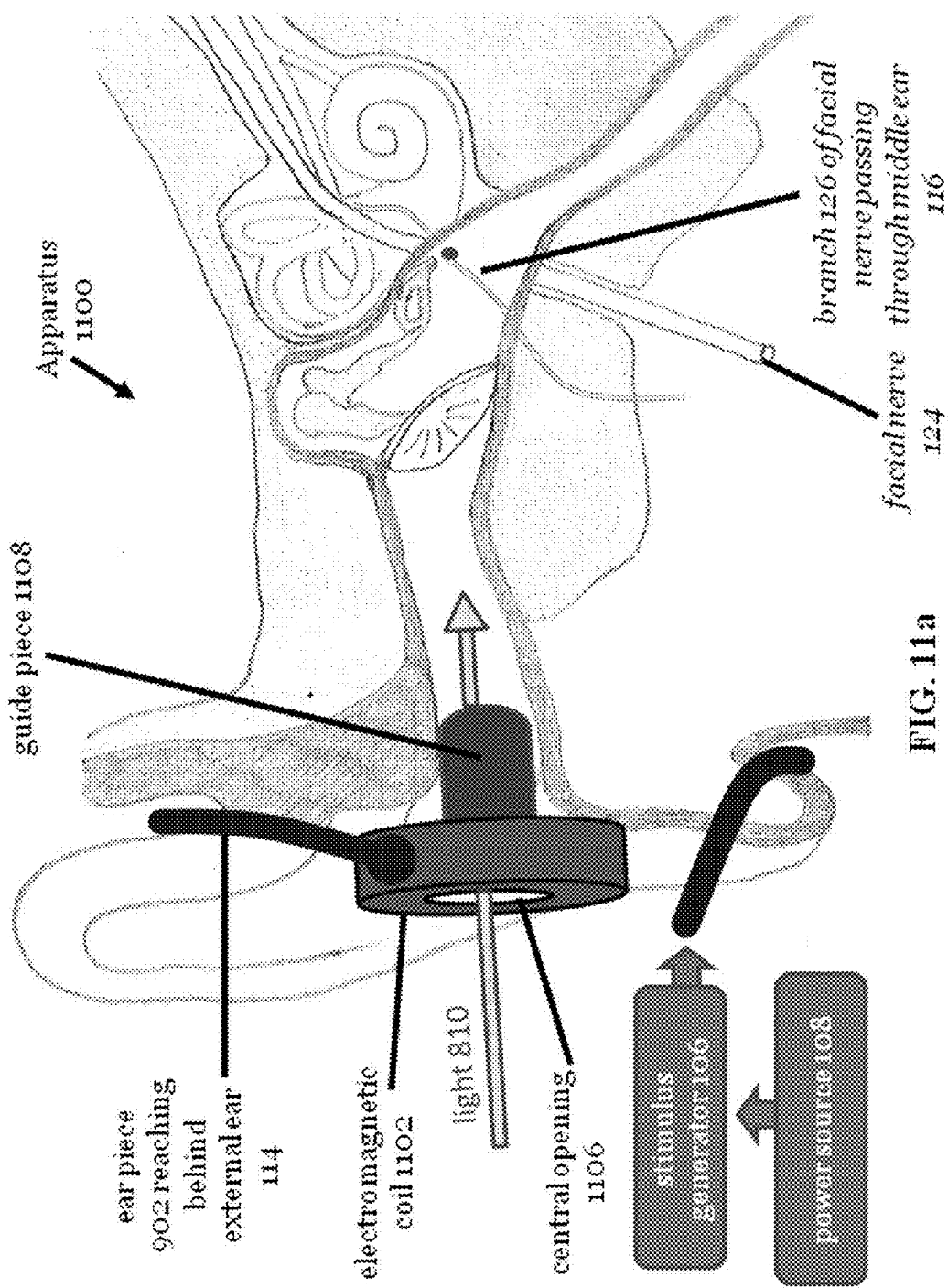
FIG. 11a depicts a side, cross-sectional view of an ear piece of the apparatus in which an electromagnetic coil forms the stimulus generator placed on the external ear, in which a guide piece positions the device over the ear canal, according to an embodiment of the invention.

FIG. 11a illustrates a side view of apparatus 1100 with an electromagnetic coil 1102 resting against the external ear 114, according to an embodiment of the invention. The coil 1102 has a central opening 1106 through which light 810 and sound can be transmitted. The electromagnetic coil 1102 is worn against the external ear using an ear piece. This ear piece can be similar to ear piece 902 (including connecting directly to the stimulus generator 106 which connects directly to the power source 108), as is shown in FIG. 10, or can be designed in a different manner as desired. In some embodiments, the apparatus can include the wireless transmitter/receiver design of FIG. 9, in which the ear piece 902 does not connect directly to the power source 108, but is worn as apparatus 900 is worn. The electromagnetic coil 1102 acts as the stimulus generator in this embodiment, and provides the stimulus energy by producing an electromagnetic field 202 through which one or more components of the facial nerve system are stimulated.

In some embodiments, the electromagnetic coil 1102 is shaped largely as a circle or ring, as shown in FIG. 11a. In other embodiments, the electromagnetic coil 1102 is shaped as a figure-8, a cloverleaf, or other configuration. A detachable connection between the distal ear piece 902 and the stimulus generator 106 allows for attachment of various configurations of the electromagnetic coil 1102. In some embodiments, the electromagnetic coil 1102 is between 2 cm and 8 cm in diameter.

In some embodiments, there is a guide piece 1108 attached to the electromagnetic coil 1102, where the guide piece is inserted into the ear canal 122 when the electromagnetic coil is placed against the external ear 114. For example, the insertable guide piece 1108 can be a sound-dampening ear plug or a speculum for visualization of the tympanic membrane 136. In some embodiments, the guide piece 1108 is positioned on the electromagnetic coil 1102 in a manner that orients the generated electromagnetic field 202 in a certain direction. In some embodiments, the guide piece 1108 is composed of ferromagnetic material that distorts or modifies the electric or magnetic field generated by the electromagnetic coil 1102 in a desirable manner. In some embodiments, the guide piece 1108 includes one or more fiducial markers that indicate the expected direction or position of the electromagnetic field 202 on an imaging study.

Figure 11B:
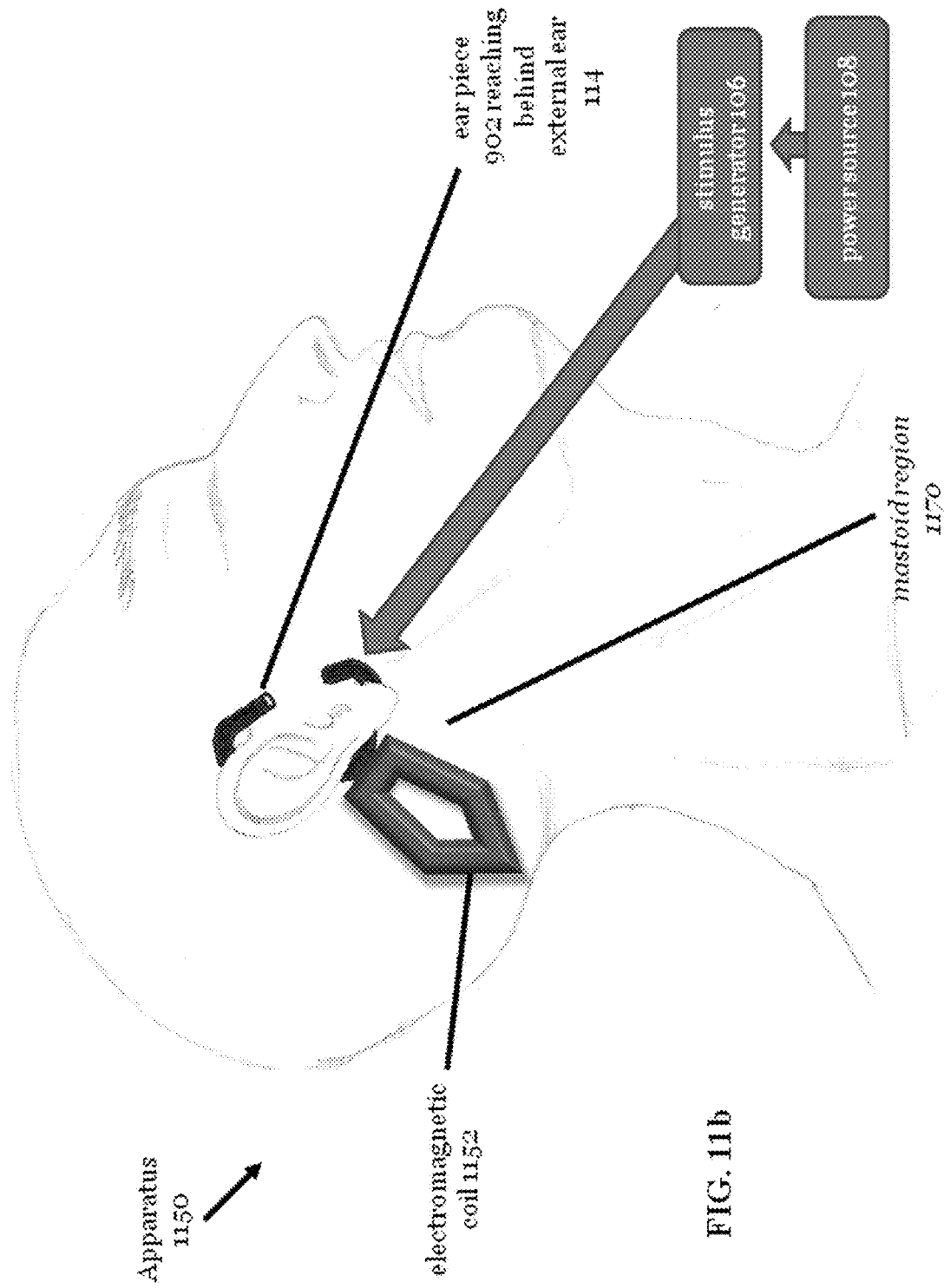
FIG. 11b depicts an ear piece of the apparatus that positions an electromagnetic coil in a manner offset from the ear canal, according to an embodiment of the invention.

As shown in FIG. 11b, some embodiments of the apparatus 1150 involve offsetting the electromagnetic coil 1152 from a position immediately over the ear canal in a manner determined by its attachment to the ear piece 902. FIG. 11b shows an electromagnetic coil 1152 shaped largely like an elongated pentagon in which attachment to the ear piece 902 at a position behind the external ear 114 places the electromagnetic coil 1152 over or near to the mastoid region 1170, above the temporal bone. As in FIG. 11a, the electromagnetic coil 1152 in this embodiment acts as the stimulus generator, and provides the stimulus energy by producing an electromagnetic field through which one or more components of the facial nerve system are stimulated. In some embodiments, the electromagnetic coil 1152 is connected through the ear piece 902 to the stimulus generator 106 which connects directly to the power source 108.

Figure 12A:
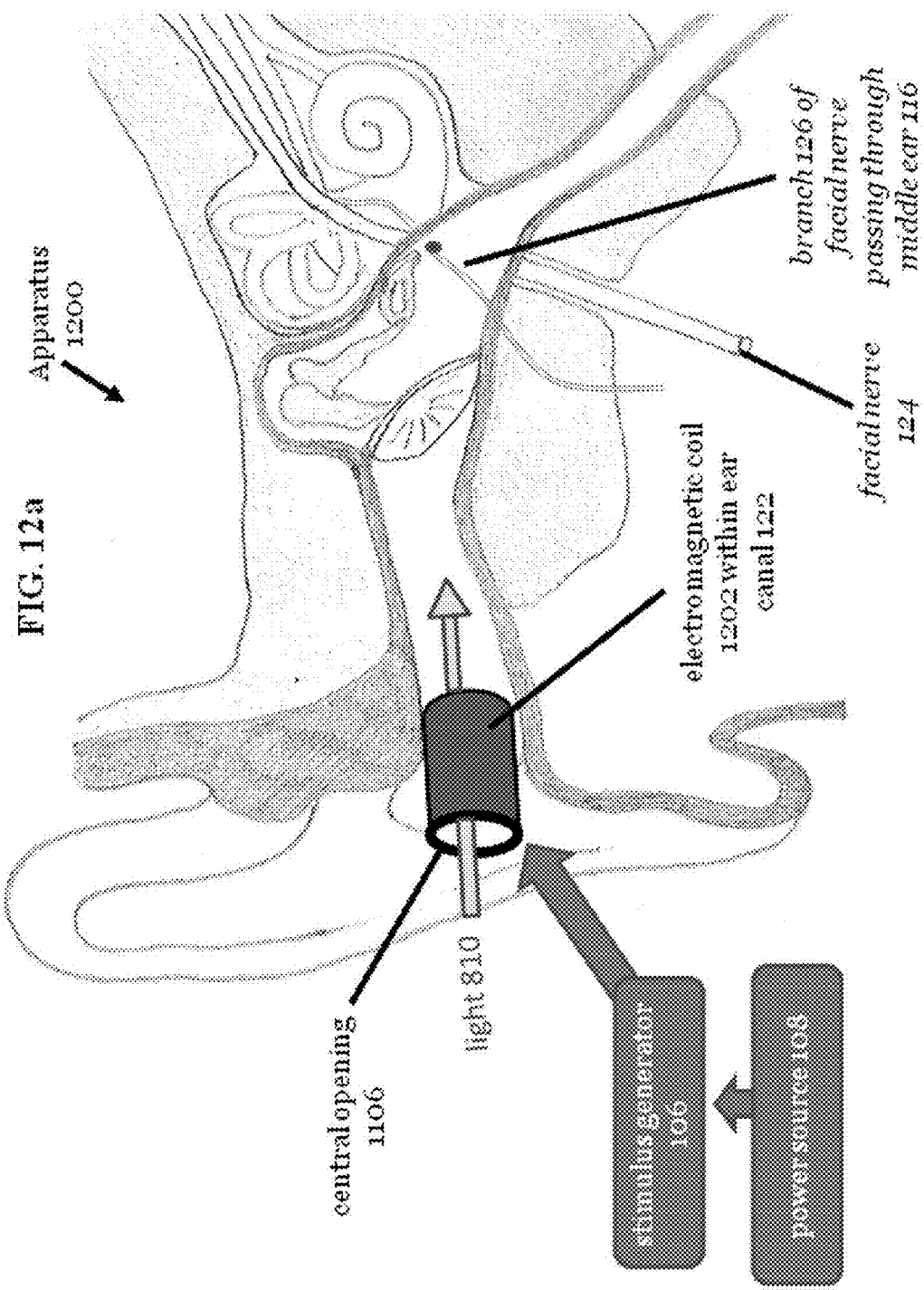
FIG. 12a depicts a side, cross-sectional view of an electromagnetic coil cylinder of the apparatus that is positioned in the ear canal by its form-fitting shape, according to an embodiment of the invention.

FIG. 12a illustrates a side view of apparatus 1200 with an electromagnetic coil 1202 resting partially or completely inside the ear canal 122, according to an embodiment of the invention. The coil 1202 has a central opening 1106 through which light 810 and sound can be transmitted. This design is similar to FIG. 11a except that the coil 1202 forms a column that rests in, is wedged in, or is surgically attached to or implanted into the ear canal 122. The electromagnetic coil 1202 can further connect directly to the stimulus generator 106 which connects directly to the power source 108. In some embodiments, the apparatus 1200 can include the wireless transmitter/receiver design of FIG. 9. As with FIG. 11a, the electromagnetic coil 1202 of FIG. 12a acts as the stimulus generator and electrode in this embodiment, and provides the stimulus energy by producing an electromagnetic field 202 that stimulates one or more components of the facial nerve system.

Figure 12B:
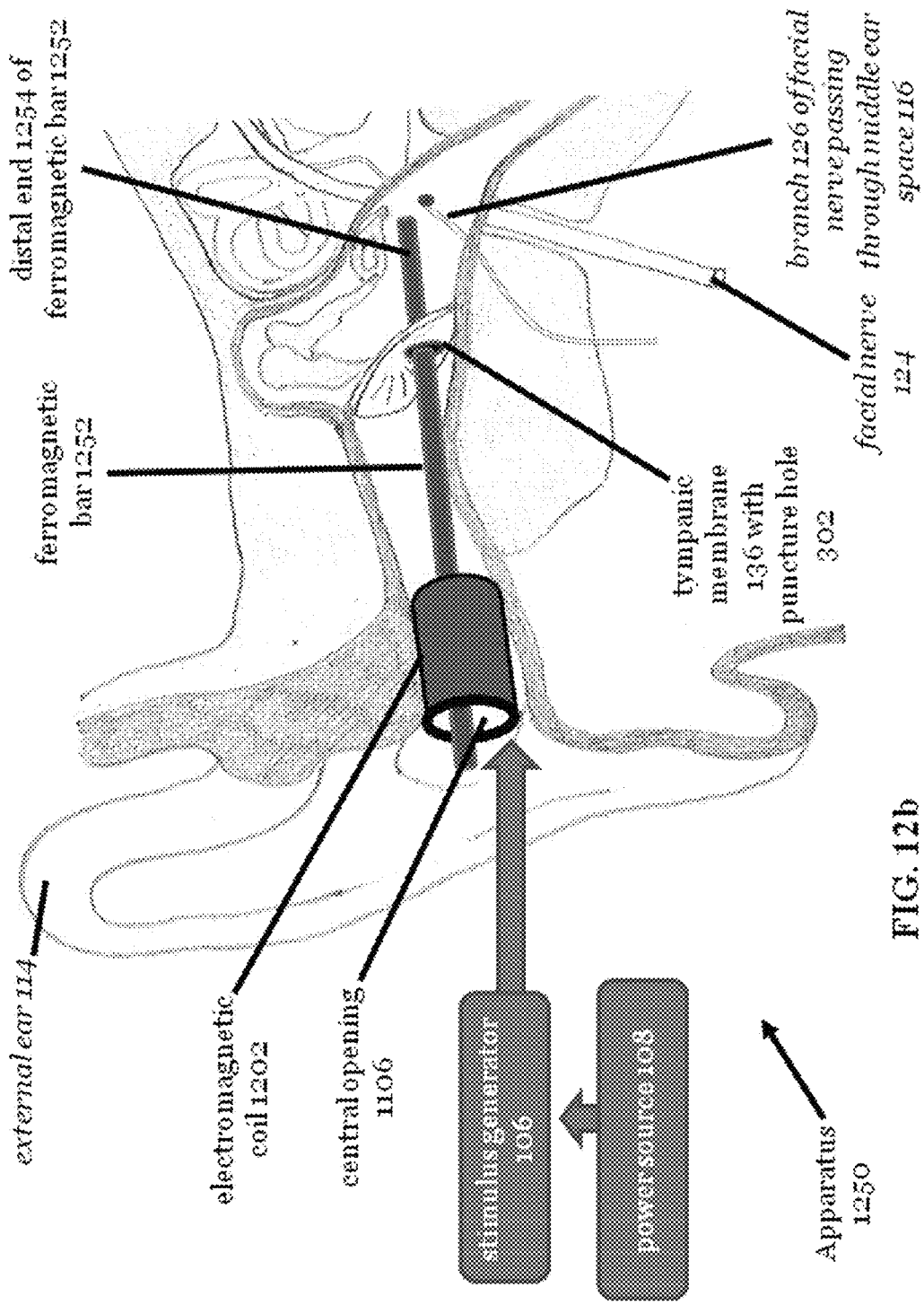
FIG. 12b depicts the electromagnetic coil cylinder of FIG. 12a with a ferromagnetic bar placed through its lumen and into the middle ear space, according to an embodiment of the invention.
Figure 12C:
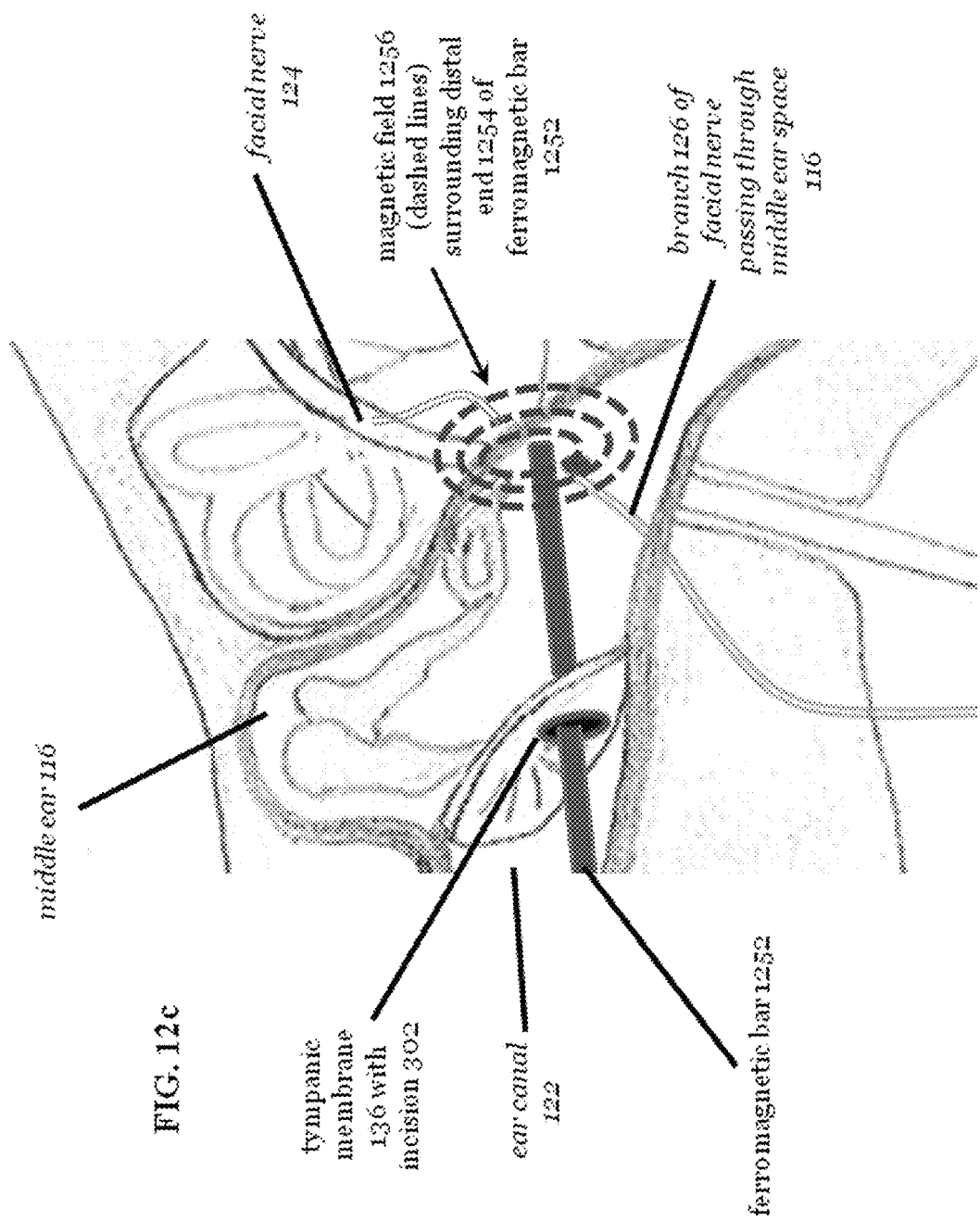
FIG. 12c depicts a side, cross-sectional view of the ear (enlargement of FIG. 12b) including stimulation by the ferromagnetic bar, according to an embodiment of the invention.

FIG. 12b illustrates a side view of apparatus 1250 in which an electromagnetic coil 1202 is placed in the ear canal 122 without use of a supporting ear piece, inflatable cuff, or other similar positioning assistance, but rather is kept in position by its form-fitting shape. In some embodiments, a ferromagnetic bar 1252 is placed within the central opening 1106 of the electromagnetic coil 1202 such that magnetic energy is conducted through the ferromagnetic bar 1252 to its distal end 1254. As illustrated in FIG. 12c, placement of the distal end 1254 of the ferromagnetic bar 1252 near the facial nerve 124 as the nerve courses behind the middle ear 116 space allows for generation of a magnetic field 1256 surrounding the distal end 1254 that then stimulates the facial nerve 124. This placement involves advancing the distal end 1254 of the ferromagnetic bar 1252 into the middle ear 116 through an incision 302 in the tympanic membrane 136. In some embodiments, the ferromagnetic bar 1252 has a 180-degree bend within the electromagnetic coil 1202 so that the proximal and distal ends of the ferromagnetic bar 1252 are brought into proximity in an elongated "horseshoe" structure (not shown). In some embodiments, the ferromagnetic bar is composed of Permalloy or Mu-metal. In some embodiments, the magnetic field carried by the ferromagnetic bar is focused or amplified by placement of ferromagnetic material in the facial nerve canal, fallopian aqueduct, or middle ear space.

Atherosclerotic disease of the cerebral arteries narrows cerebral arteries, which may chronically impair blood flow to parts of the brain, thereby causing among other symptoms recurring near-strokes/transient ischemic attacks as blood flow becomes intermittently compromised. In order to overcome the narrowing in the cerebral arteries caused by atherosclerosis or other malformations, chronic stimulation of the facial nerve system provided by a chronic treatment device can be used to maintain dilation of the arteries, thereby preventing stroke caused by atherosclerotic disease.

Figure 13:
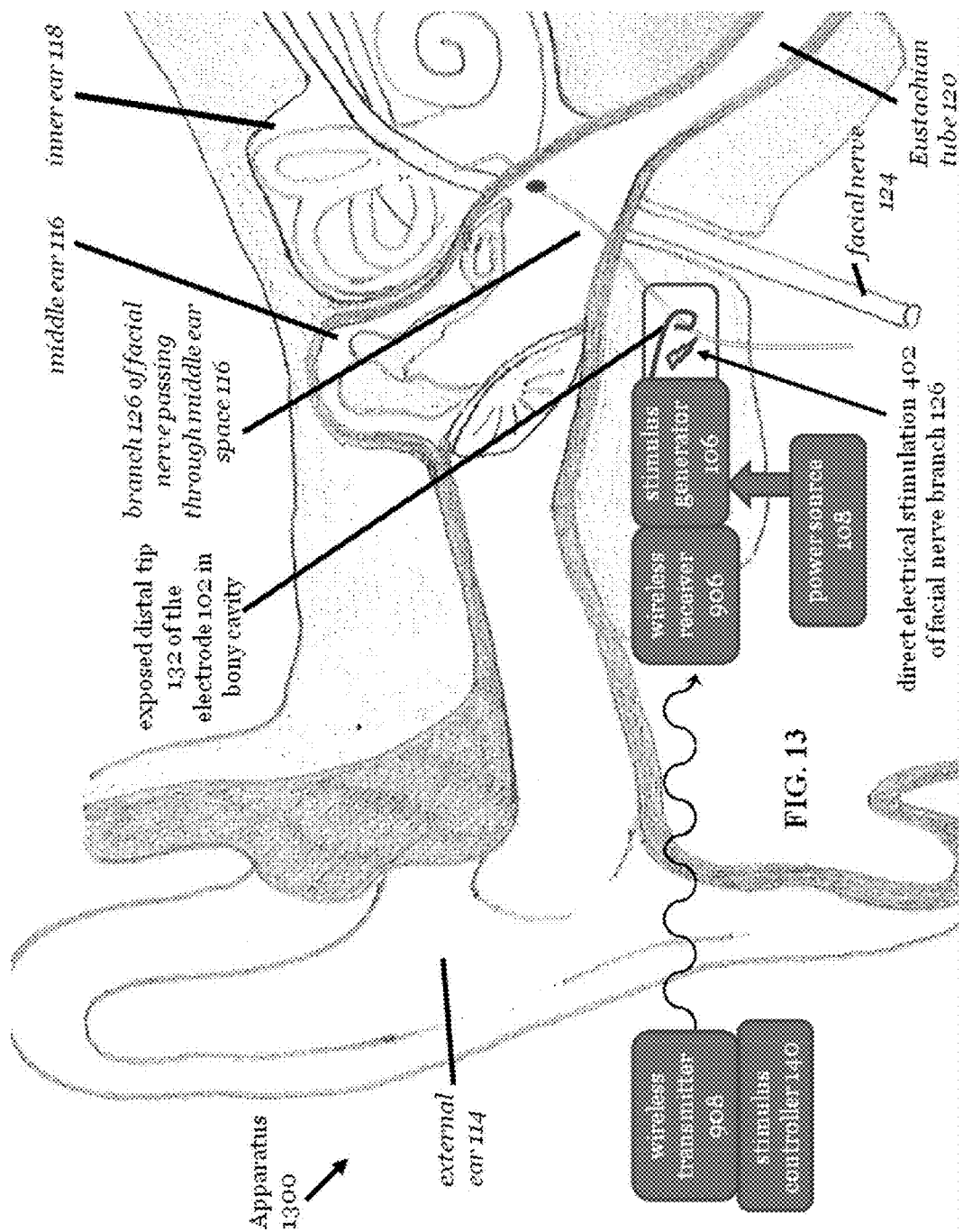
FIG. 13 depicts a side, cross-sectional view of a stimulator device for chronic modulation of the facial nerve system implanted into the bones of the skull, according to an embodiment of the invention.

FIG. 13 illustrates a side view of apparatus 1300 with the electrode 102 chronically positioned within the bone of the skull and/or soft tissues of the head for stimulation of one or more components of the facial nerve system, according to an embodiment of the invention. In some embodiments, the electrode 102 is positioned in proximity to a branch 126 of the facial nerve 124 that passes through the middle ear space 116. Stimulation can then be achieved by application of electrical current from a stimulus generator 106. In some embodiments, the stimulus generator 106 and power source 108 are implanted within the body, thereby allowing direct connection between the electrode 102 and the stimulus generator 106. Also implanted in the body is a power source 108 that is connected directly to the stimulus generator 106 by one or more wires or other connectors. In some embodiments, a stimulus controller 140 controls one or more parameters of the stimulus energy applied to the electrode 102 by the stimulus generator 906 using a wireless transmitter 908 external to the body that transmits information to a wireless receiver 906 connected to the stimulus generator 106 where the wireless receiver 906 is implanted within the body.

Figure 14:
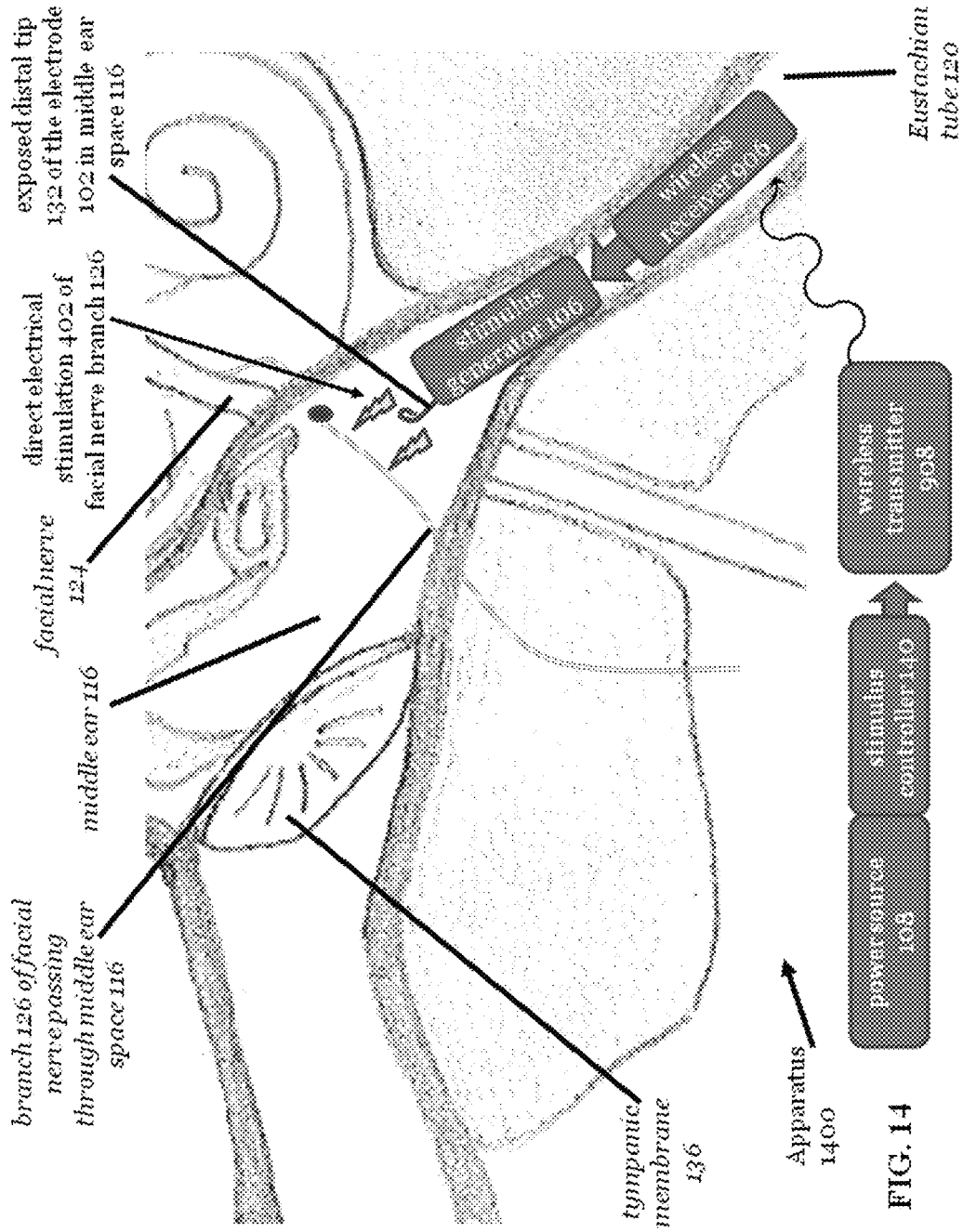
FIG. 14 depicts a side, cross-sectional view of a stimulator device for chronic modulation of the facial nerve system placed into the middle ear, according to an embodiment of the invention.

FIG. 14 illustrates a side view of apparatus 1400 with the electrode 102 positioned within the middle ear 116 by means of the Eustachian tube 120 for stimulation of one or more components of the facial nerve system, according to an embodiment of the invention. In some embodiments, the electrode 102 is in direct connection with a stimulus generator 106 placed within the middle ear 116 or the Eustachian tube 120. Stimulus energy from a power source 108 with parameters determined by a stimulus controller 140 can be provided to the stimulus generator 106 either by direct connection between the stimulus controller 140 and the stimulus generator 106 through the Eustachian tube (not shown) or wirelessly by transmission of the stimulus energy from a wireless transmitter 908 placed external to the body to a wireless receiver 906 that is in direct connection with the stimulus generator 906. In other embodiments, a wireless transmitter 908 is an aural appliance (not shown) configured to fit against the external ear 114. Circuitry in the wireless transmitter 908 can drive the wireless transmitter 908 to transmit stimulus energy to the wireless receiver 906. Similarly, circuitry in the wireless receiver 906 can receive the stimulus energy and transmit the energy to the stimulus generator 106. The apparatus 1400 positioned in the middle ear 116 in this manner and supplied with stimulus energy by wireless transmission can be used for acute or chronic treatment of a disorder of abnormal blood flow within the head. Electrical stimulation 402 of a branch 126 of the facial nerve can be performed, as in this example, or other means of stimulation can be employed. In other embodiments, direct connection of the stimulus generator 106 and the stimulus controller 140 can be maintained by one or more wires running through the Eustachian tube 120 and exiting the head via nasal or oral passages.

Neural Structure Modulation Methods

Figure 15:
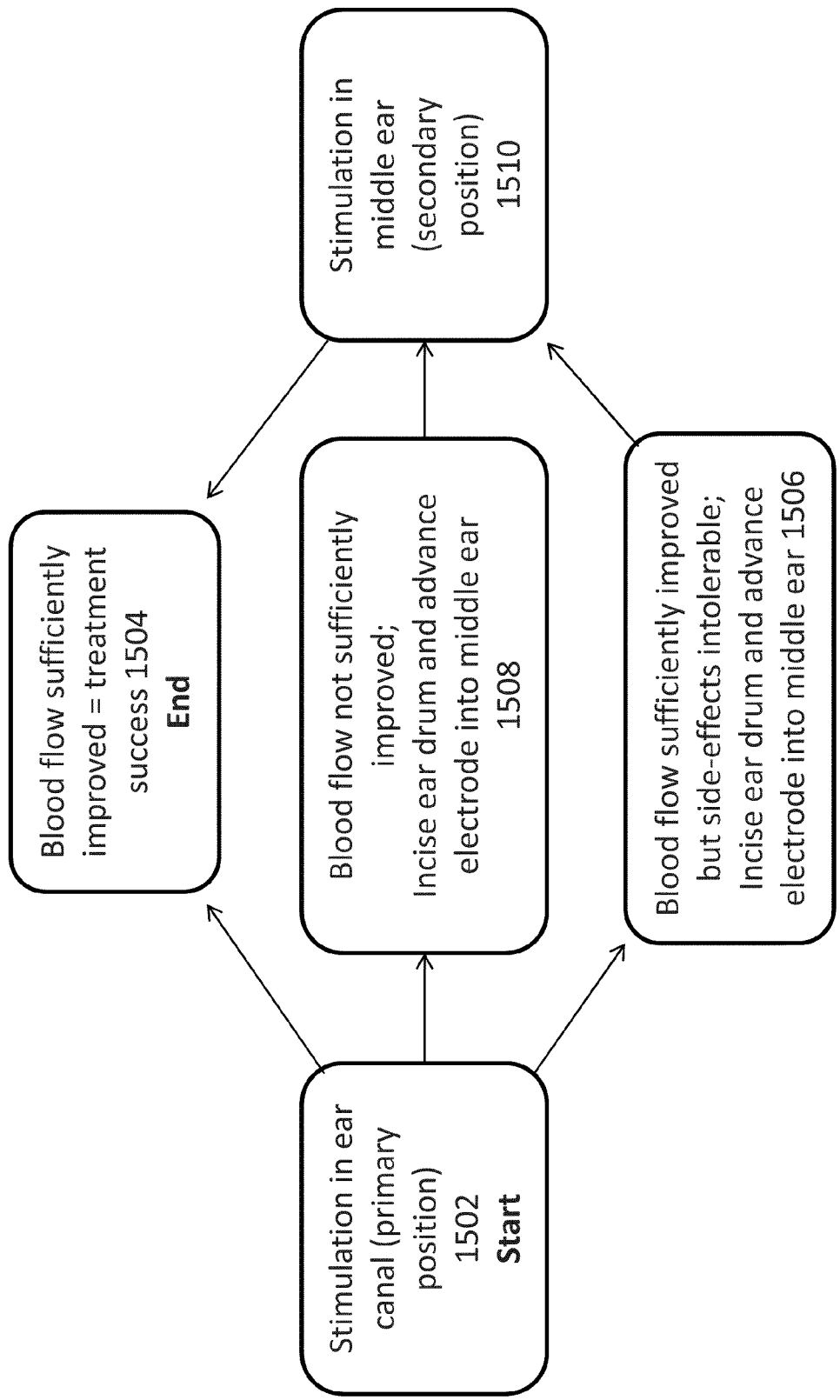
FIG. 15 is a flow diagram illustrating a method for stimulation of neural structures, according to an embodiment of the invention.

Referring now to FIG. 15, there is shown a flow diagram providing a method for neural structure modulation, according to an embodiment of the invention. It should be understood that these steps are illustrative only. Different methods of the invention may perform the illustrated steps in different orders, omit certain steps, and/or perform additional steps not shown in FIG. 15 (the same is true for the other Figures). The method can start and end at various points in the process, and often the method is a continuous process with multiple steps occurring simultaneously, so the Figures provide only an example of one ordering of method steps. In addition, the method can be performed using any of the apparatuses described herein or another apparatus capable of performing the steps provided below.

As shown in FIG. 15, the method includes a step of providing stimulation 1502 in the ear canal (primary position). For example, the stimulation can include providing stimulus energy to an electrode positioned in the ear canal, in the primary position for the apparatus. This may result in sufficiently improving 1504 blood flow to the brain, thus rendering the treatment of the stroke a success. However, stimulation in the primary position may not be successful for one of two reasons. First, stimulation 1508 in the primary position may not sufficiently improve blood flow to the brain, thus rendering the treatment of the stroke a failure. Second, even if blood flow to the brain is sufficiently improved by stimulation in the primary position, side effects associated with stimulation in the primary position may prevent the use of stimulation in the primary position 1506. In case of failure of stimulation in the primary position, the method can further include a step of advancing an electrode into the middle ear by puncturing the tympanic membrane and inserting the electrode through the punctured tympanic membrane. The method can also include providing stimulation 1510 from this position in the middle ear, which is the secondary position for the apparatus. In this secondary position, the electrode is closer to some components of the facial nerve system for providing stimulation to improve blood flow, and certain components of the facial nerve system can be directly stimulated with electrical current. The stimulation 1510 provided from the secondary position may result in sufficiently improving 1504 blood flow, thus rendering the treatment of the stroke a success. Thus, in the embodiment of FIG. 15, the method includes first trying to stimulate the facial nerve system from the primary position (in the ear canal), and if this position does not provide the desired results, the method includes then trying to stimulate the facial nerve system from the secondary position (in the middle ear). However, the user does not have to perform the steps in this order, or may perform only one of the steps. For example, only the secondary position may be used if this is preferred.

Figure 16:
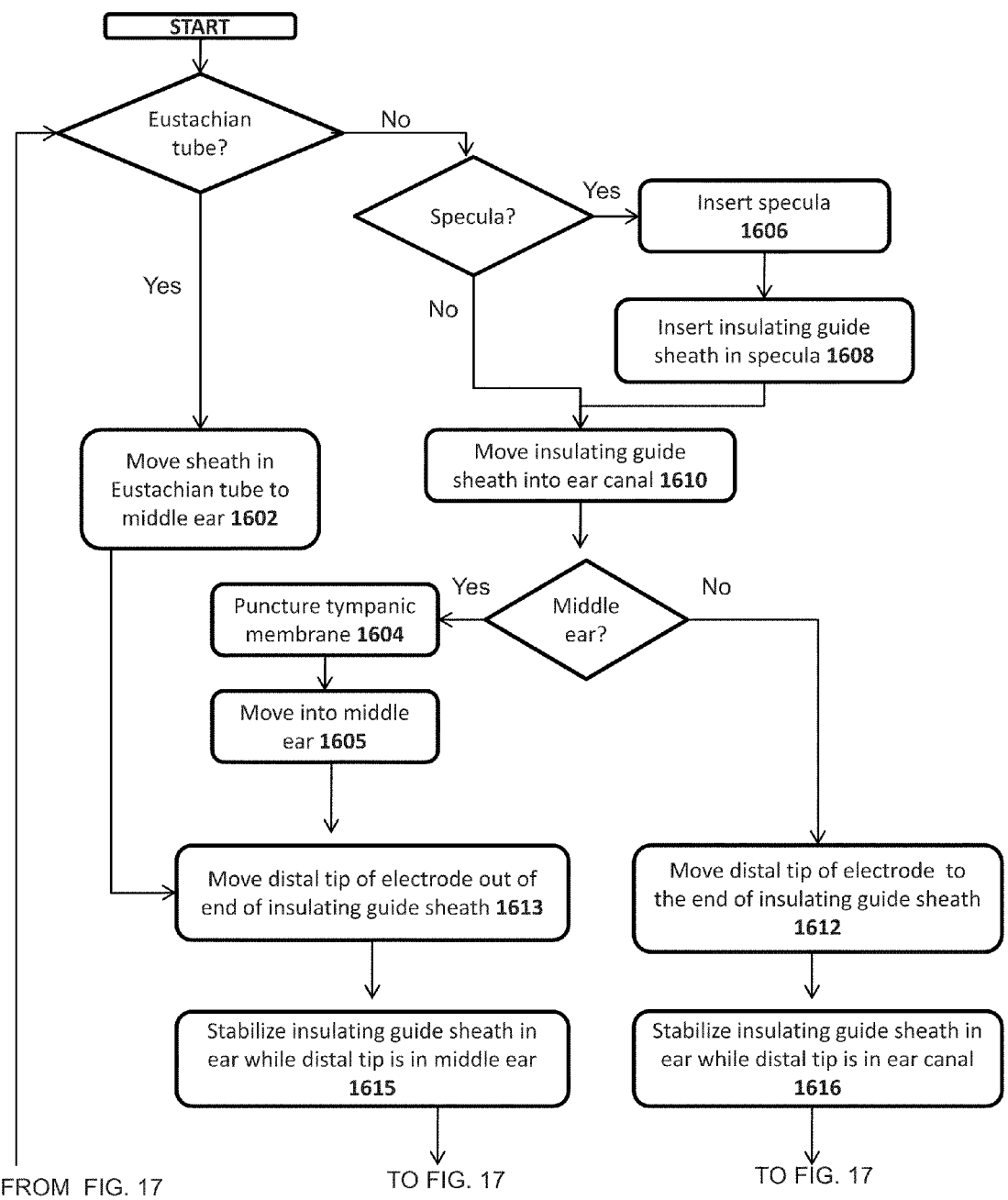
FIG. 16 is a flow diagram illustrating another method for stimulation of neural structures, according to an embodiment of the invention.

Referring now to FIG. 16, there is shown a method of facial nerve system stimulation, according to an embodiment of the invention. If the means for first approaching the stimulation site will be via the Eustachian tube of the ear (e.g., due to poor access through the ear canal), the method includes moving 1602 the insulating guide sheath within a Eustachian tube of the ear to an internal side of the tympanic membrane. This method then continues to a step that includes moving 1613 the electrode within the insulating guide sheath (note that the moving 1602 of the insulating guide sheath and moving 1613 of the electrode can occur simultaneously). If the mechanism for approaching the stimulation site will not be via the Eustachian tube (e.g., will be via the ear canal), then the method follows a different course in the flowchart. If a speculum is to be used, the speculum is inserted 1606 into the ear canal, and the insulating guide sheath is inserted 1608 into the speculum. For example, the insulating guide sheath can be inserted 1608 through a groove or peripheral channel along the lateral length of a specialized otoscope speculum and then into the ear canal of the subject under direct visualization of anatomical structures within the ear. If no speculum is to be used, the insulating guide sheath is moved 1610 into the ear canal without a speculum. The moving 1610 of the insulating guide sheath into the ear can include moving the insulating guide sheath into the ear canal and into proximity of the tympanic membrane.

Once the device has been moved 1610 into the ear canal, the user can opt to proceed with stimulation from the ear canal (primary position), or can opt to advance the device into the middle ear to perform the stimulation in the middle ear (secondary position). If the stimulation is to occur in the middle ear, the moving 1610 of the insulating guide sheath into the ear can lead to steps of puncturing 1604 the tympanic membrane with the insulating guide sheath (e.g., a sharpened distal tip of the insulating guide sheath) or other surgical procedure and moving 1605 the insulating guide sheath into the middle ear. In some embodiments, the user might opt to first provide stimulation from the ear canal, and if the appropriate response does not occur, the user can then opt to move the device into the middle ear for providing stimulation in the middle ear.

With successful placement of the distal end of the insulating guide sheath in the middle ear or with placement of the distal end of the insulating guide sheath in the ear canal external to the tympanic membrane, the method further includes moving 1612 the distal tip of the electrode within the insulating guide sheath to the end of the insulating guide sheath (for stimulation in the primary position) or moving 1613 the distal tip of the electrode out of the distal end of the insulating guide sheath (for stimulation in the secondary position). This can also occur simultaneously with the any of the steps described above or it may precede any of the steps in certain methods. In the primary position, the distal tip of the electrode can remain inside the insulating guide sheath in a position near the external side of the tympanic membrane and in the secondary position, the distal tip can be exposed near an internal side of the tympanic membrane. The method also includes stabilizing 1615 the insulating guide sheath to hold the insulating guide sheath in place within the ear while the distal tip of the insulating guide sheath is located in the middle ear, or stabilizing 1616 the insulating guide sheath to hold the insulating guide sheath in place within the ear while the distal tip of the insulating guide sheath is located in the ear canal. Stabilizing 1615,1616 can include inflating an inflatable cuff associated with the outer wall of the insulating guide sheath to fit the insulating guide sheath against a surface of the ear or to hold the insulating guide sheath in place within the ear canal. Stabilizing 1615,1616 can further include stabilization with an ear piece fixed to the external ear.

Figure 17:
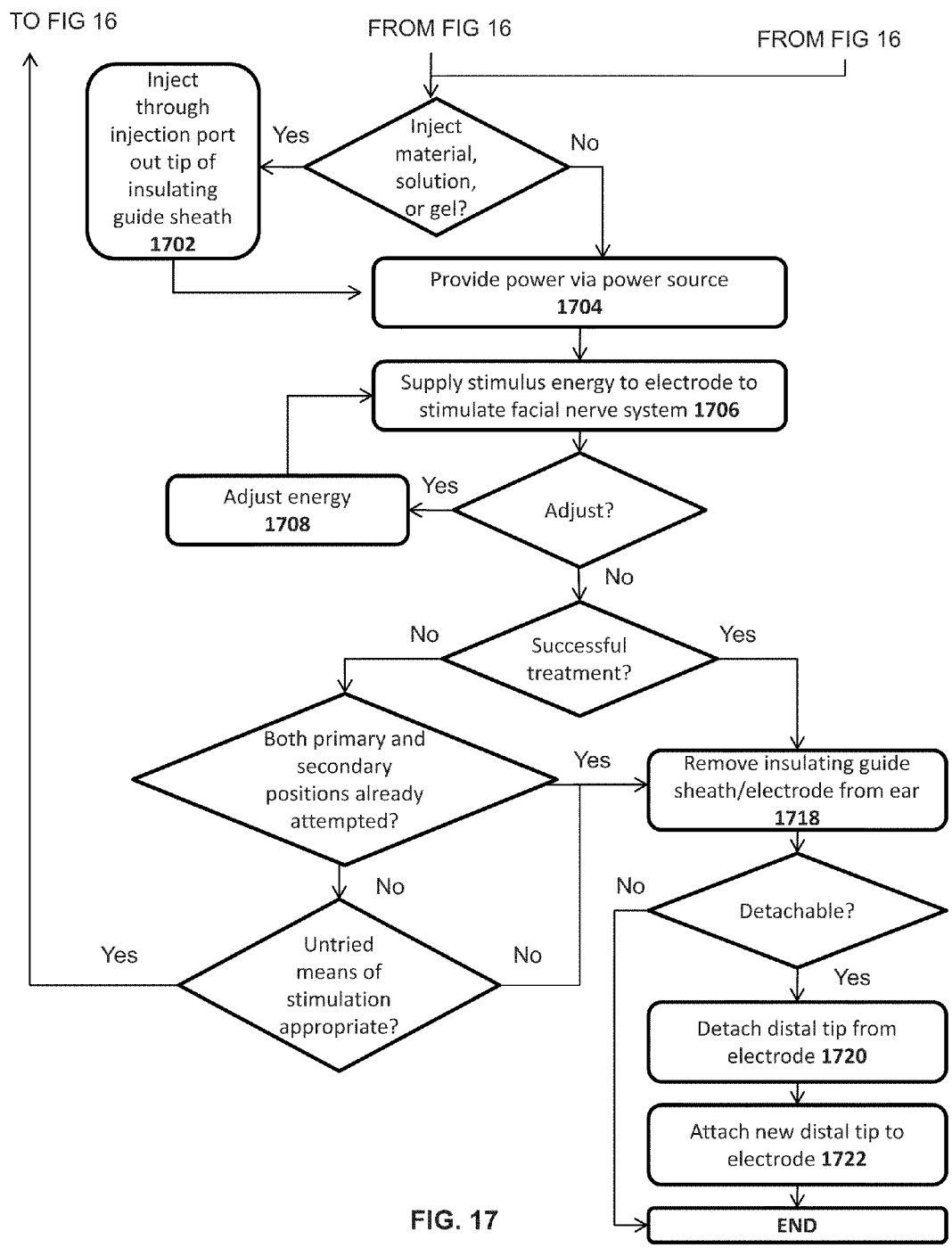
FIG. 17 is a flow diagram illustrating a continuation of the method for stimulation of neural structures of FIG. 16, according to an embodiment of the invention.

Referring now to FIG. 17, there is shown a continuation of the flow chart of FIG. 16, according to an embodiment of the invention. If a material, gel, or solution (e.g., electrically-conductive gel or solution to increase conductivity, an anesthetic or other pharmacological agent to eliminate an unwanted response of tissue local to the electrode, etc.) is to be injected into the insulating guide sheath, the method includes injecting 1702 such material, gel, or solution through an injection port out the distal tip of the insulating guide sheath to facilitate treatment of the subject. This can also occur earlier or later in the process, or at multiple times in the process with the same or different materials, gels, or solutions, as desired. The material, gel, or solution can be released from the distal end of the insulating guide sheath into an ear canal, middle ear, or Eustachian tube.

The method also includes providing 1704 power via a power source for supplying the stimulus energy to the electrode (the power may also be provided 1704 automatically, as the device may be constantly connected to or in communication with the power source). The power can be provided 1704 via wires connecting the power source to the device, or wirelessly via a wireless transmitter/receiver. In addition, the method includes supplying 1706 stimulus energy to the electrode to stimulate one or more components of the facial nerve system in the vicinity of the ear (e.g., a facial nerve, a tympanic plexus, a geniculate ganglion, a tympanic plexus, a sphenopalatine nerve or ganglion, a petrosal nerve, etc.). In some methods, supplying 1706 stimulus energy to the electrode modulates blood flow to the brain of the subject or enhances delivery of a blood-borne pharmacologic agent to treat stroke or another condition of the subject. The stimulus energy can be supplied via a wire connecting a stimulus generator to the electrode or wirelessly via a stimulus generator that is not in direct contact with the electrode. Where the electrode is in the primary position (in the ear canal), supplying 1706 stimulus energy can create an electromagnetic, electric, or magnetic field to stimulate the facial nerve system from the external side of the tympanic membrane. Where the electrode is in the secondary position (in the middle ear), an electrical current can be directly supplied to components of the facial nerve system within the middle ear and may also be provided to certain components of the facial nerve system indirectly (e.g., via an electromagnetic field). In some methods, supplying 1706 stimulus energy drives electrical current between a cathodic site and an anodal site of a bipolar electrode. In some embodiments, supplying 1706 stimulus energy drives electrical current from a monopolar electrode to a ground wire applied to the pinna of the ipsilateral or contralateral ear, or to another part of the head.

If any adjustments are needed or desired regarding the stimulus energy, the method can include adjusting 1708 the stimulus energy. For example, the adjustments can be made based on physiological or pathophysiological responses of the subject to the stimulus energy. The method can continue with supplying 1706 and adjusting 1708 as needed until the method is done. When the method is done (i.e., the treatment is successful and complete), the insulating guide sheath and/or electrode can be removed 1718 from the ear. If the device has a detachable electrode tip, the method can include detaching 1720 the tip and attaching 1722 a new tip.

If the method is not finished because successful treatment was not achieved and because appropriate stimulation in both the primary and secondary positions was not attempted, the method can continue to completion with steps 1602, 1604, 1605, 1606, 1608, 1610, 1613, 1615, 1702, 1704, 1706, 1708, 1718, 1720, and/or 1722, described above. For example, if the device was initially used in the primary position in the ear canal, but the secondary position was not attempted, the device can then be moved into the secondary position in the middle ear if stimulation in the middle ear is judged appropriate.

Figure 18:
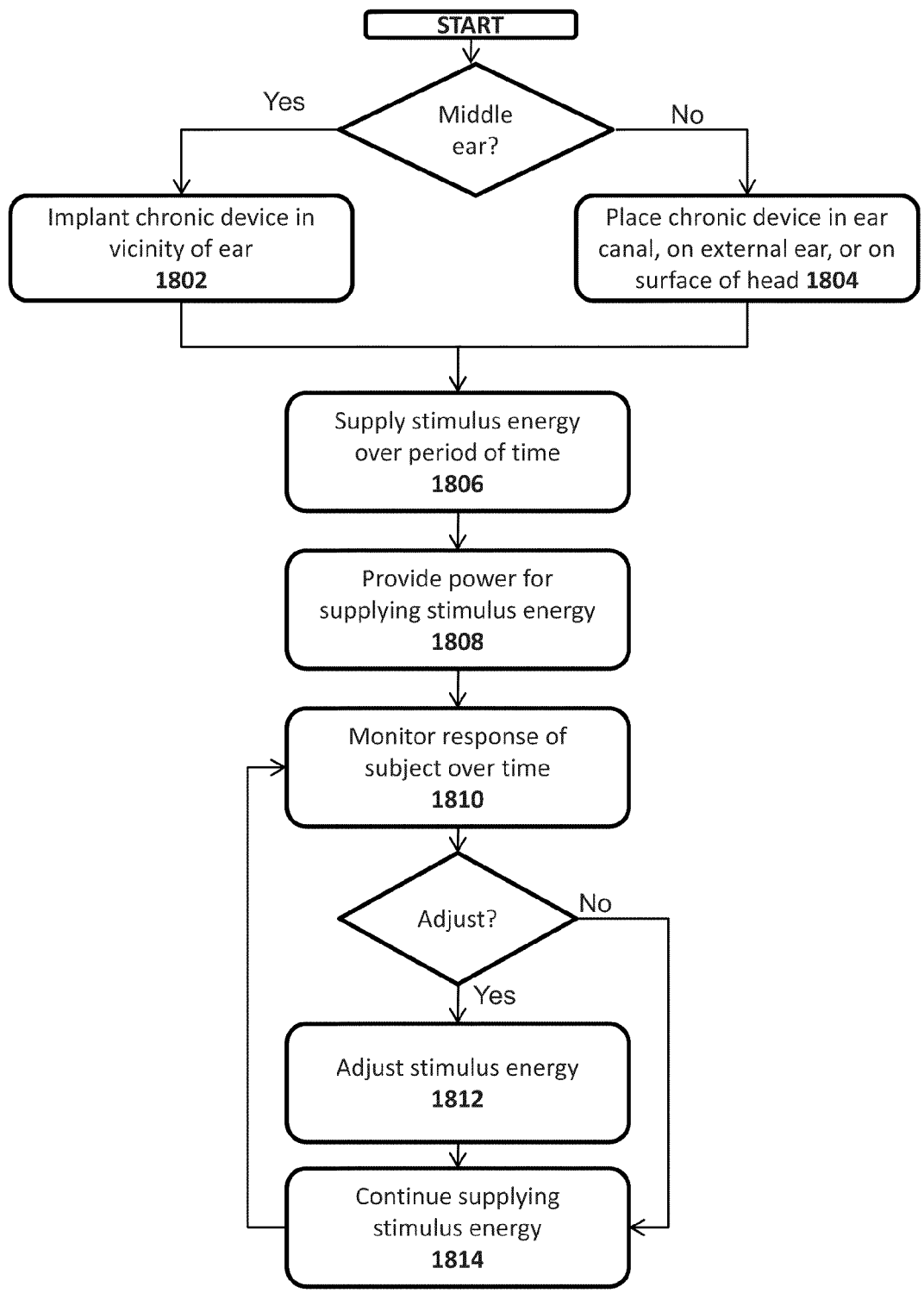
FIG. 18 is a flow diagram illustrating a chronic method for stimulation of neural structures, according to an embodiment of the invention.

Referring now to FIG. 18, there is shown a method of chronic nerve stimulation, according to an embodiment of the invention. If the method is to occur in the middle ear, the method includes surgically, interventionally, or endoscopically implanting 1802 the chronic treatment device (e.g., an electrode with or without an insulating sheath) within or in proximity to the ear of the subject. This may include placement of the chronic treatment device in the middle ear space, in the Eustachian tube, into a bone of the skull, or into a soft tissue or potential space of the head. If the method is not to involve implanting 1802 the chronic treatment device, and instead will occur in the ear canal, the external ear, or on the surface of the head, the method includes placing 1804 the chronic treatment device into the ear canal, on the external ear, or on the surface of the head (e.g., the mastoid region behind the external ear) of the subject. Certain positions may only allow for stimulation of one or more components of the limited facial nerve system. In some methods, the device can be implanted into the facial nerve canal, the Eustachian tube, the internal auditory meatus, the Fallopian aqueduct, the mastoid antrum, the temporal bone, the cartilage of the ear, or the epitympanic recess of the subject. The method also includes supplying 1806 stimulation (e.g., via a stimulus generator that can be in wireless communication with the electrode) to the electrode over a period of time to chronically stimulate one or more components of the facial nerve system in the vicinity of the ear. In some methods, the supplying 1806 of stimulation step includes supplying stimulation automatically over a period of time to maintain relaxation of one or more cerebral or carotid arteries associated with the facial nerve system for treatment or prevention of a stroke, particularly stroke caused by atherosclerotic disease. The method can further include providing 1808 power via a power source for supplying the stimulus energy to the electrode.

The method can also include monitoring 1810 one or more physiological or pathophysiological responses of the subject over a period of time. In this method, if it is determined that an adjustment is needed, the method can include adjusting 1812 the intensity, frequency, etc. of the stimulus energy supplied to the electrode. The adjustment 1812 can be made based on the one or more physiological or pathophysiological responses of the subject, or based on other factors. In some methods, the adjustment 1812 can also occur automatically without requiring any action by a physician or subject to make the adjustment. In other embodiments, the physician or subject can have access to the monitored 1810 responses of the subject, and can control the adjustment 1812 based on the monitoring 1810. The method can include continued supplying 1814 of stimulus energy to the electrode with periodic monitoring 1810 and adjusting 1812 as needed over a period of time to chronically treat the subject. In this manner, if stimulation is needed or desired of one or more components of the facial nerve system to dilate vessels and prevent stroke, the chronic device can provide such stimulation. This can be done automatically or under the control of a physician or of the subject using the device.

Various of the features described herein for the different apparatus designs can be used with other apparatus designs as well. In addition, the numerical values presented herein are approximate, and can include numbers below or above the stated values. Furthermore, the numerical ranges presented herein can include any of the values, fractional values, or ranges falling within the numerical range. While the present teachings are described in conjunction with various embodiments and methods, it is not intended that the present teachings be limited to such embodiments. On the contrary, the present teachings encompass various alternatives, modifications, and equivalents, as will be appreciated by those of skill in the art. Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise. In addition, number labels included in the drawings are organized to provide clarity. In some cases, the same number label is used throughout to refer to a structure that corresponds with another structure in a different apparatus design of a different figure, even though that structure may be somewhat differently designed or have some different components, a different size or shape, etc. For example, insulating guide sheath 104, electrode 102, and distal tip 132 are given the same number labels throughout. In some cases, a different number label is used to delineate corresponding structures across different apparatus designs, even though that structure may be generally designed the same or have the same components, size or shape, etc.

What is claimed is:
1. An apparatus, comprising:
an insulating guide sheath moveable toward and away from an ear of a mammalian subject, the insulating guide sheath including a guide piece that is configured to enter an ear canal of the mammalian subject, and an external portion that is attached to the guide piece and that is configured to be placed against an external ear of the mammalian subject, the guide piece and the external portion being axially aligned;

a coil with elongated ends enclosed within the external portion of the insulating guide sheath, wherein the coil is disposed to be placed in proximity to the ear while within the external portion by insertion of the guide piece within the ear canal to position the external portion against the external ear;

a stimulus generator in electrical communication with the coil through the elongated ends for supplying current to the coil such that the current flowing through the coil generates a stimulating magnetic field from the coil, wherein:

the guide piece within the ear canal is configured to position the external portion containing the coil such that the stimulating magnetic field from the coil is oriented toward the ear canal for stimulating a neural structure of a facial nerve system of the mammalian subject through the ear, the guide piece encloses a magnetic material and has a length that is perpendicular to a plane of the coil, the magnetic material configured to shape, amplify, or focus the stimulating magnetic field generated by the coil within the ear canal, and the coil, the external portion of the insulating guide sheath surrounding the coil, the guide piece, and the magnetic material have axially aligned central openings that are penetrable to light and sound; and a power source in electrical communication with the stimulus generator for providing power to the stimulus generator for supplying the current to the coil.

2. The apparatus of claim 1, wherein the stimulus generator is further configured for applying a current to the coil sufficient to stimulate the facial nerve system in the vicinity of the ear.

3. The apparatus of claim 1, further comprising a stimulus controller attached to the stimulus generator for adjusting the current to the coil based on one or more physiological or pathophysiological responses of the subject, the responses selected from the group consisting of: taste sensation; audition; lacrimation; nasal drainage; nasal congestion; salivation; sound sensitivity; face, head, or hand movements; speech production or arrest; sensation of body movement; eye movements; cranial blood flow; direct or indirect activity of a nerve; and severity of neurological dysfunction of the subject.

4. The apparatus of claim 1, further comprising a stimulus controller attached to the stimulus generator for adjusting the current to the coil for activating the neural structure of the facial nerve system to improve blood flow to the brain of the subject or to enhance delivery of a blood-borne pharmacologic agent to treat stroke or another condition of the subject.

5. The apparatus of claim 1, further comprising a specialized speculum insertable into the ear of the subject, the speculum having an opening through which light can be transmitted to allow direct visualization of an anatomical structure within the ear.

6. The apparatus of claim 1, further comprising one or more leads connecting the stimulus generator to the coil.

7. The apparatus of claim 1, wherein the stimulus generator further comprises a wireless transmitter and a wireless receiver, the wireless transmitter being located outside of a body of the subject and at least a portion of the wireless receiver being electrically coupled to the coil, wherein the wireless transmitter is configured for wirelessly transmitting instructions to the wireless receiver to supply the current to the coil.

8. The apparatus of claim 7, wherein the wireless receiver and the wireless transmitter are electromagnetically or inductively coupled.

9. The apparatus of claim 7, further comprising:

one or more wires electrically coupling the power source to the wireless transmitter;

circuitry in the wireless transmitter to drive the wireless transmitter to transmit a stimulus energy to the wireless receiver; and circuitry in the wireless receiver adapted to receive the stimulus energy and apply the current to the coil.

10. The apparatus of claim 1, further comprising an ear piece attached to the insulating guide sheath and configured to reach around the ear to hold the insulating guide sheath against the external ear.

11. The apparatus of claim 1, wherein the guide piece is a sound-dampening ear plug.

12. The apparatus of claim 1, wherein the guide piece of the insulating guide sheath is configured to fit against a surface within the ear canal for holding the external portion of the insulating guide sheath against the external ear of the mammalian subject such that the coil is held perpendicular to an axis of the ear canal.

13. The apparatus of claim 1, wherein the coil is circular- or ring-shaped.

14. The apparatus of claim 1, wherein the coil is figure-8- or cloverleaf-shaped.

15. The apparatus of claim 1, wherein a length of the guide piece is such that the guide piece extends into the ear canal to a distance that is less than half a length of the ear canal.

16. The apparatus of claim 1, wherein a circumference of the guide piece is such that the guide piece is in contact with an internal surface of the ear canal around the circumference of the guide piece.

17. The apparatus of claim 1, wherein a diameter of the external portion of the insulating guide sheath is greater than a diameter of an opening to the ear canal.

18. The apparatus of claim 1, wherein the elongated ends of the coil comprise a current inflow wire and a current outflow wire that terminate in the coil.

19. The apparatus of claim 1, wherein the insulating guide sheath is designed to insulate the coil with elongated ends from the ear of the subject while current is supplied to the coil.

* * * * *